United States Patent
Baldwin et al.

(10) Patent No.: US 7,763,013 B2
(45) Date of Patent: Jul. 27, 2010

(54) SWABABLE FLUID CONNECTORS AND FLUID CONNECTOR PAIRS

(75) Inventors: Brian Eugene Baldwin, Centennial, CO (US); Randall Wallace Smith, Lakewood, CO (US); Gregory John Baldwin, Greenwood Village, CO (US)

(73) Assignee: Baxa Corporation, Englewood, CO (US)

( * ) Notice: Subject to any disclaimer, the term of this patent is extended or adjusted under 35 U.S.C. 154(b) by 0 days.

(21) Appl. No.: 12/135,596

(22) Filed: Jun. 9, 2008

(65) Prior Publication Data

US 2008/0264450 A1 Oct. 30, 2008

Related U.S. Application Data

(63) Continuation of application No. 11/036,644, filed on Jan. 14, 2005, now Pat. No. 7,396,051.

(51) Int. Cl.
*A61M 25/16* (2006.01)
(52) U.S. Cl. .............. 604/533; 604/256; 604/905; 285/354
(58) Field of Classification Search ............ 285/354, 285/386; 604/533, 241, 905, 249, 256
See application file for complete search history.

(56) References Cited

U.S. PATENT DOCUMENTS

| | | | |
|---|---|---|---|
| 2,968,497 A | 1/1916 | Treleman | |
| 4,256,106 A | 3/1981 | Schoor | 128/247 |
| 4,334,551 A | 6/1982 | Pfister | 137/614 |
| 4,411,656 A | 10/1983 | Cornett, III | 604/212 |
| 4,512,766 A | 4/1985 | Vailancourt | |
| 4,874,377 A | 10/1989 | Newgard et al. | |
| 5,047,021 A | 9/1991 | Utterberg | |
| 5,064,416 A | 11/1991 | Newgard et al. | |
| 5,215,538 A | 6/1993 | Larkin | |
| 5,322,518 A | 6/1994 | Schneider et al. | 604/247 |
| 5,380,306 A | 1/1995 | Brinon | |
| 5,535,785 A | 7/1996 | Werge et al. | 137/843 |
| 5,536,258 A | 7/1996 | Folden | |
| 5,549,577 A | 8/1996 | Siegel et al. | |
| 5,620,427 A | 4/1997 | Werschmidt et al. | 604/283 |
| 5,624,402 A | 4/1997 | Imbert | |
| 5,651,776 A | 7/1997 | Appling et al. | |
| 5,685,866 A | 11/1997 | Lopez | |

(Continued)

*Primary Examiner*—David E Bochna
(74) *Attorney, Agent, or Firm*—Marsh Fischmann & Breyfogle LLP

(57) ABSTRACT

A first fluid connector is provided for selective interconnection to and fluid transfer with a second fluid connector. The first connector comprises a fluid passageway, an internal member and an outer collar supportably disposed about the internal member for selective advancement and retraction relative thereto. At least a portion of the fluid passageway may extend through the internal member. The outer collar may be selectively retracted to facilitate cleaning of the internal member. In some embodiments, the outer collar and internal member may be disposed so that a distal portion of the internal member is substantially flush with or a distal portion of internal member projects beyond a distal end of the outer collar when the outer collar is in a retracted position relative thereto. To facilitate cleaning, a distal end or distal portion of the internal member may be substantially closed when the first and second connectors are disconnected. The second connector may be adapted to facilitate fluid interconnection with the first connector, and may also present a cleanable distal end when disconnected.

21 Claims, 27 Drawing Sheets

U.S. PATENT DOCUMENTS

| | | | |
|---|---|---|---|
| 5,699,821 A | 12/1997 | Paradis | 137/1 |
| 5,702,374 A | 12/1997 | Johnson | 604/283 |
| 5,756,178 A | 5/1998 | Obadia | 428/66.4 |
| 5,775,671 A | 7/1998 | Cote, Sr. | 251/149.8 |
| 5,782,816 A | 7/1998 | Werschmidt et al. | 604/256 |
| 5,788,215 A | 8/1998 | Ryan | 251/149 |
| 5,807,345 A | 9/1998 | Grabenkort | 604/199 |
| 5,851,201 A | 12/1998 | Ritger et al. | 604/240 |
| 5,855,230 A | 1/1999 | Guala et al. | 138/89 |
| 5,873,862 A | 2/1999 | Lopez | |
| 5,928,204 A | 7/1999 | Lopez | |
| 5,947,954 A | 9/1999 | Bonaldo | 604/533 |
| 5,954,313 A | 9/1999 | Ryan | 251/149 |
| 5,984,373 A | 11/1999 | Fitoussi et al. | 285/92 |
| 6,039,302 A | 3/2000 | Cote, Sr. et al. | 251/149.1 |
| 6,063,062 A | 5/2000 | Paradis | 604/249 |
| 6,113,068 A | 9/2000 | Ryan | 251/149 |
| 6,132,403 A | 10/2000 | Lopez | |
| 6,152,913 A | 11/2000 | Feith et al. | 604/533 |
| 6,158,458 A | 12/2000 | Ryan | 137/515.5 |
| 6,171,287 B1 | 1/2001 | Lynn et al. | 604/256 |
| 6,217,560 B1 | 4/2001 | Ritger et al. | 604/243 |
| RE37,357 E | 9/2001 | Lynn | 604/533 |
| 6,290,206 B1 | 9/2001 | Doyle | 251/149.1 |
| 6,332,633 B1 | 12/2001 | Fitoussi et al. | 285/332 |
| 6,364,869 B1 | 4/2002 | Bonaldo | 604/537 |
| 6,394,983 B1 | 5/2002 | Mayoral et al. | 604/192 |
| 6,447,498 B1 | 9/2002 | Jepson et al. | |
| 6,491,667 B1 | 12/2002 | Keane et al. | 604/192 |
| 6,541,802 B2 | 4/2003 | Doyle | 257/149.1 |
| 6,572,592 B1 | 6/2003 | Lopez | |
| 6,605,076 B1 | 8/2003 | Jepson et al. | |
| 6,655,655 B1 | 12/2003 | Matkovich et al. | 251/149.1 |
| 6,682,509 B2 | 1/2004 | Lopez | 604/249 |
| 6,695,829 B2 | 2/2004 | Hellstrom et al. | 604/415 |
| 6,706,022 B1 | 3/2004 | Leinsing et al. | 604/247 |
| 6,726,658 B2 | 4/2004 | Hochman | 604/164.08 |
| 6,726,672 B1 | 4/2004 | Hanly et al. | 604/414 |
| 6,740,063 B2 | 5/2004 | Lynn | 604/256 |
| 6,745,998 B2 | 6/2004 | Doyle | |
| 6,843,513 B2 | 1/2005 | Guala | |
| 6,964,406 B2 | 11/2005 | Doyle | |
| 6,994,315 B2 | 2/2006 | Ryan et al. | |
| 7,004,934 B2 * | 2/2006 | Vaillancourt | 604/533 |
| 7,056,308 B2 * | 6/2006 | Utterberg | 604/256 |
| 7,396,051 B2 * | 7/2008 | Baldwin et al. | 285/354 |

\* cited by examiner

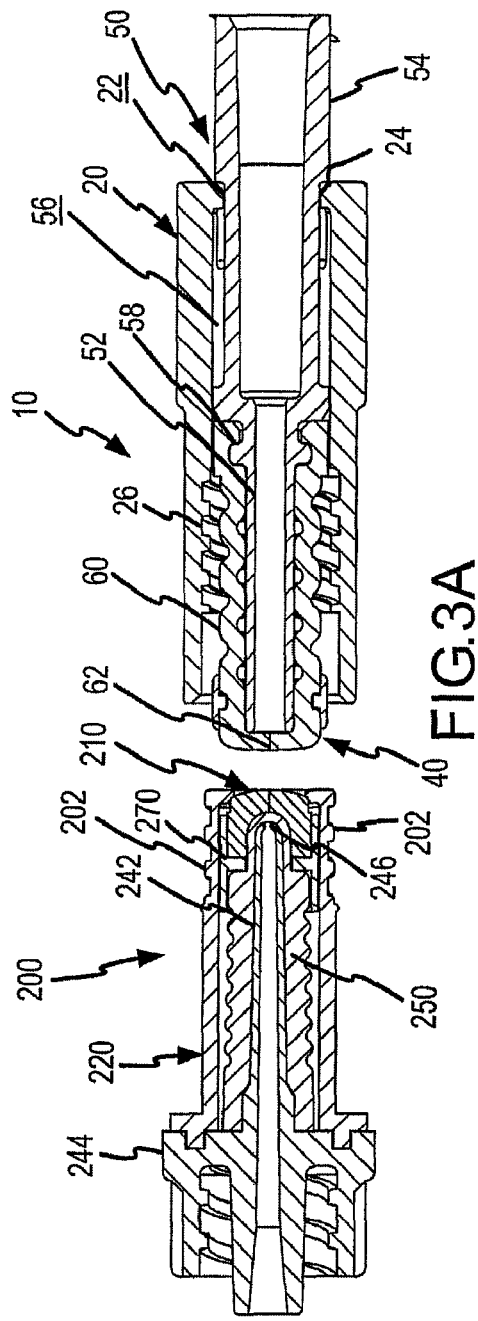
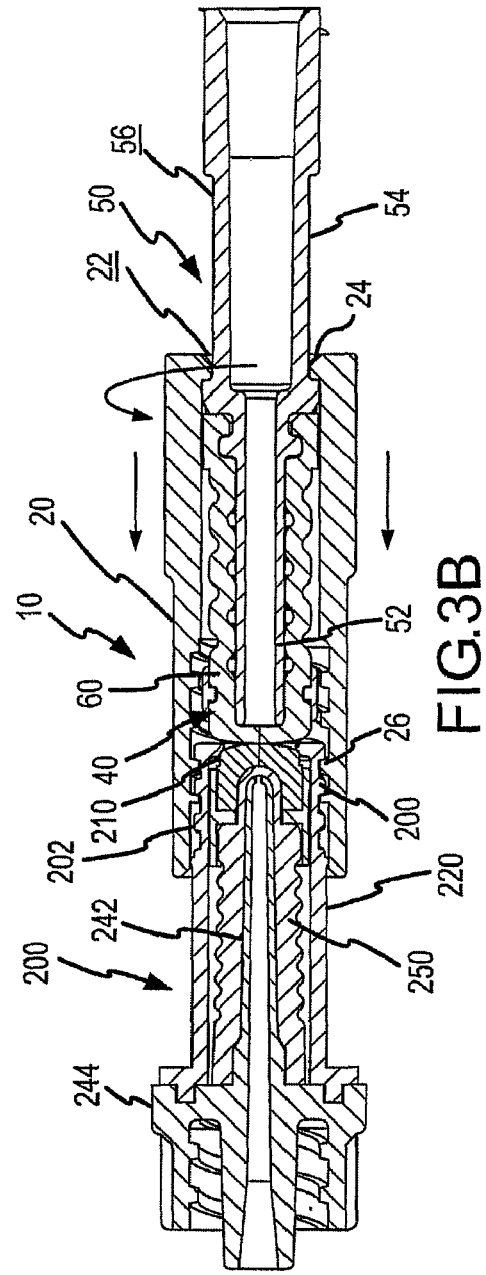
FIG.3A
FIG.3B

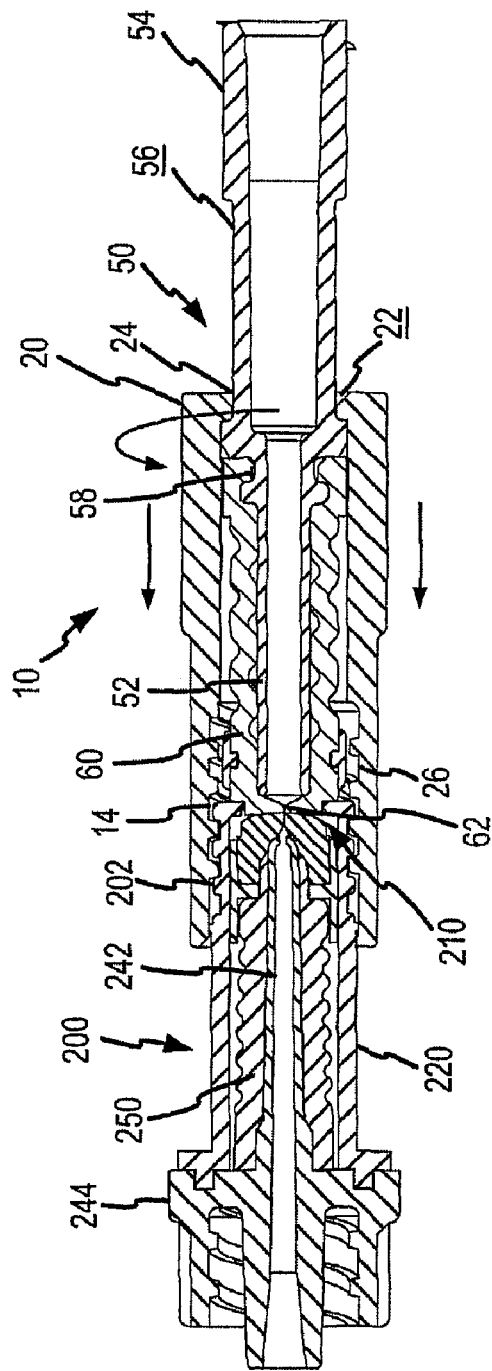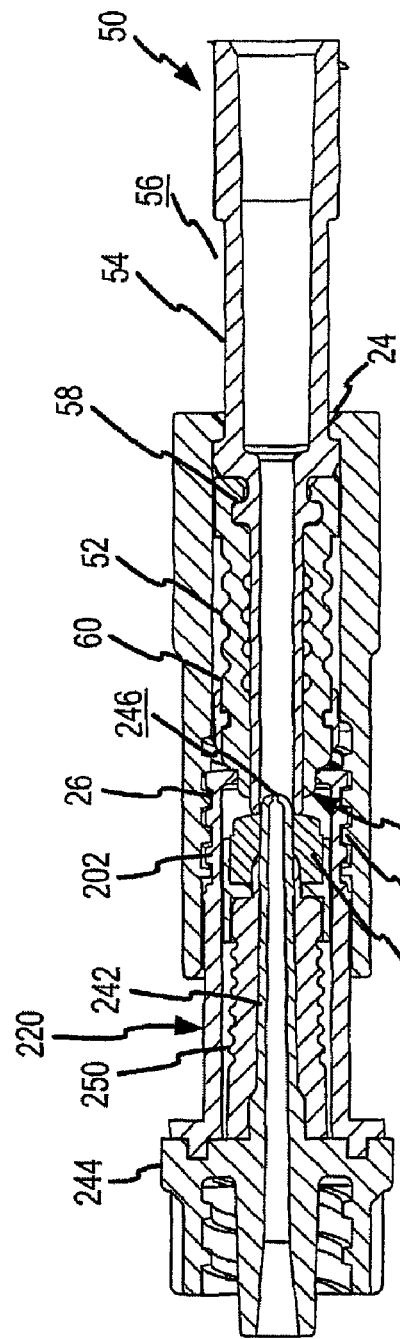
FIG.3C
FIG.3D

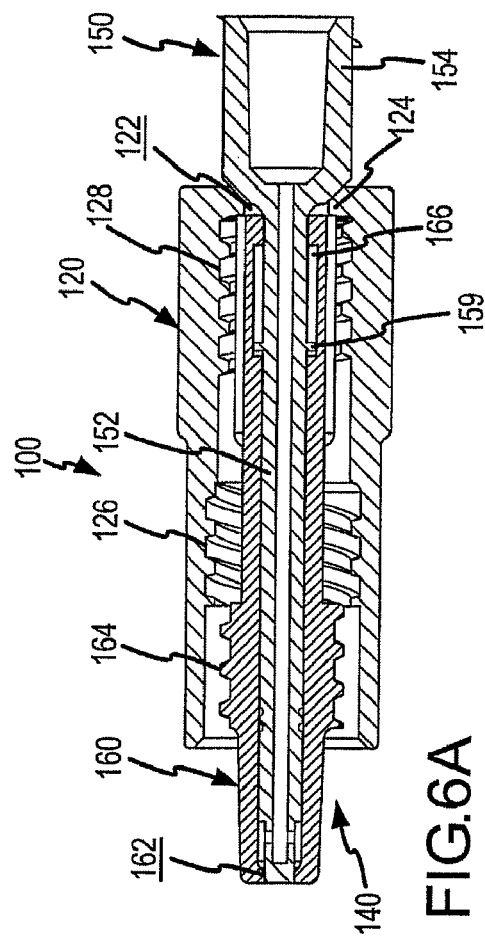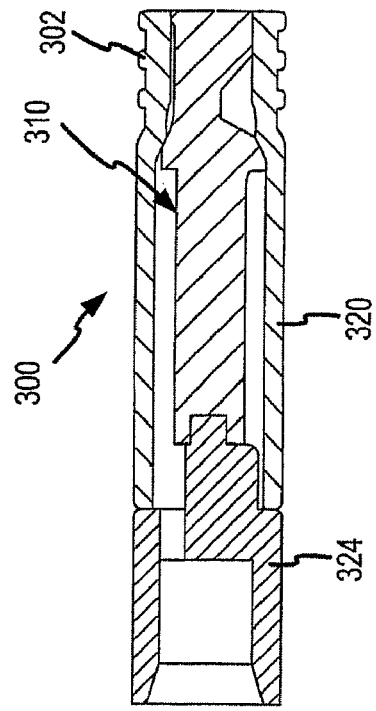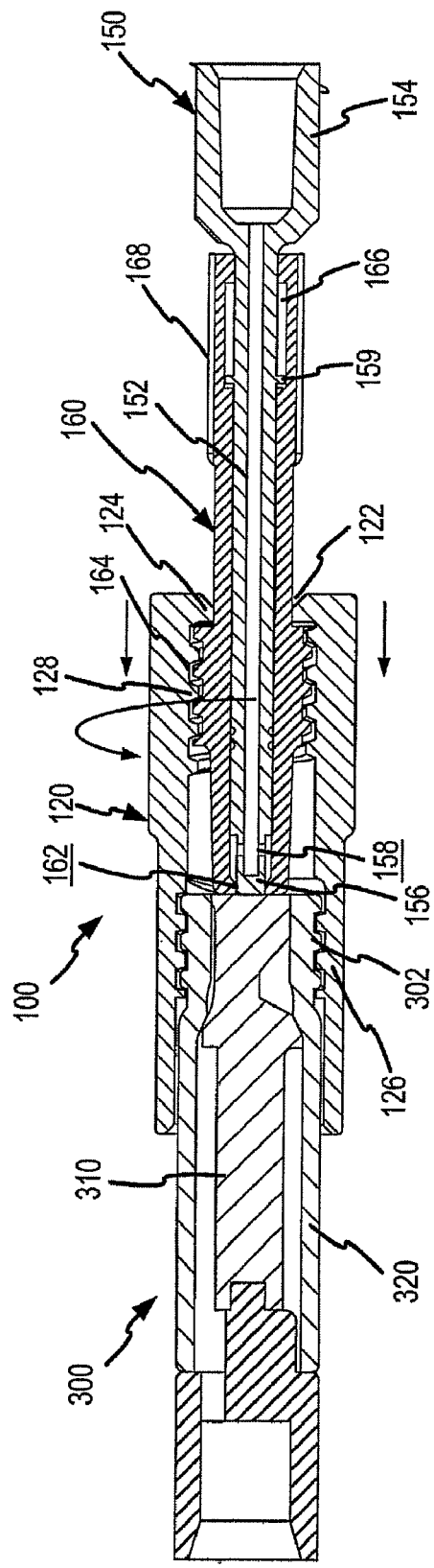
FIG.6A
FIG.6B

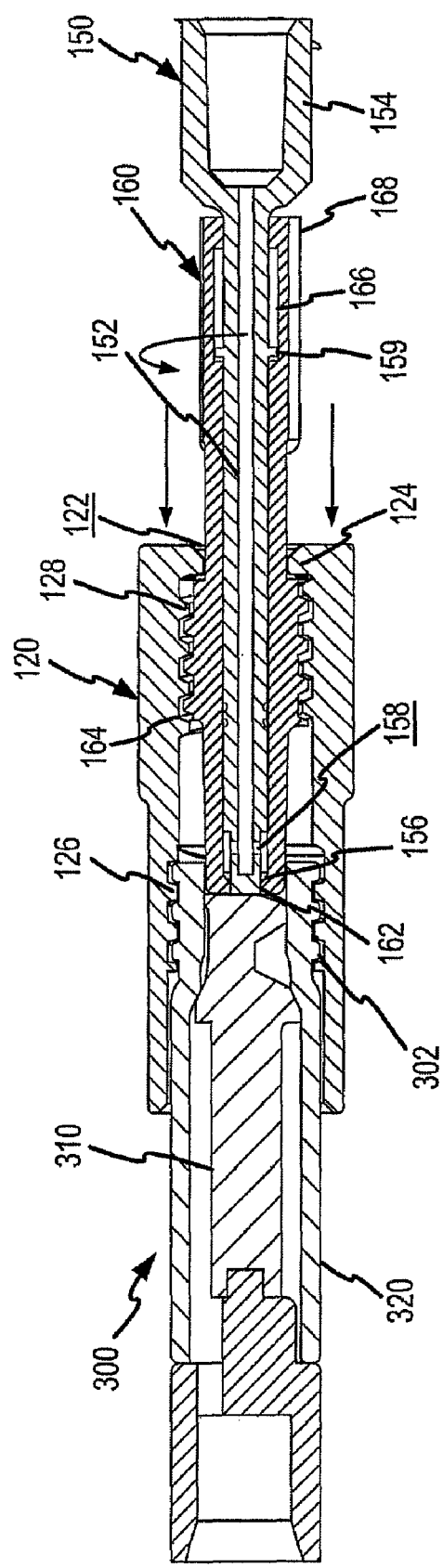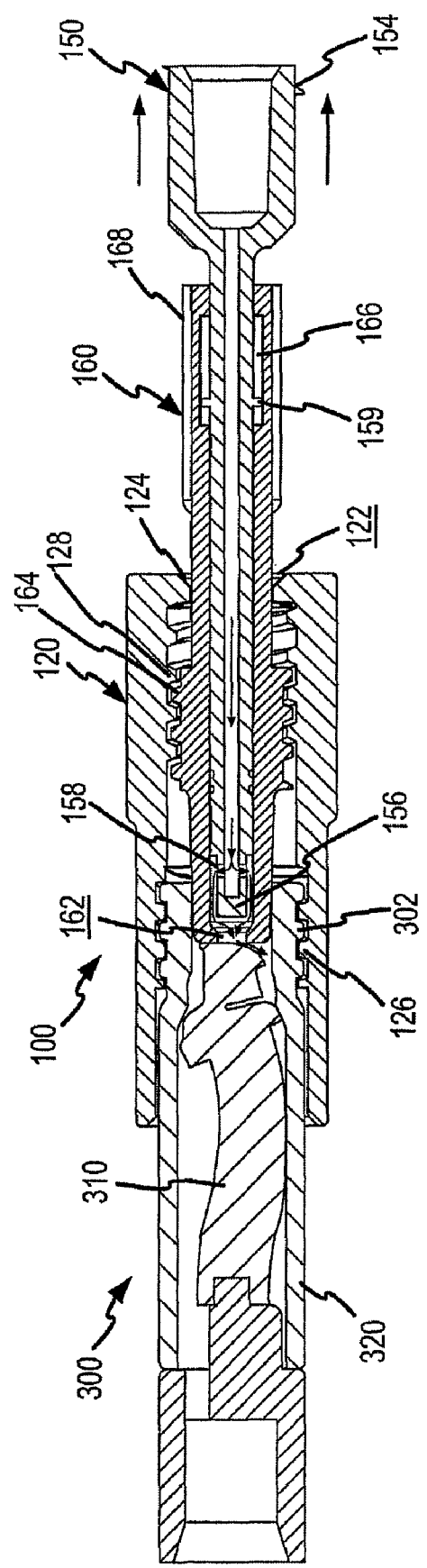

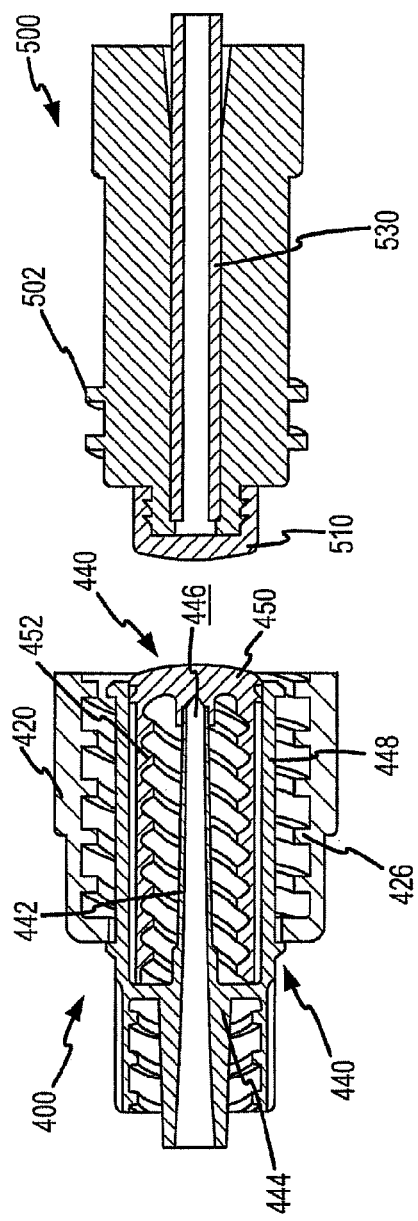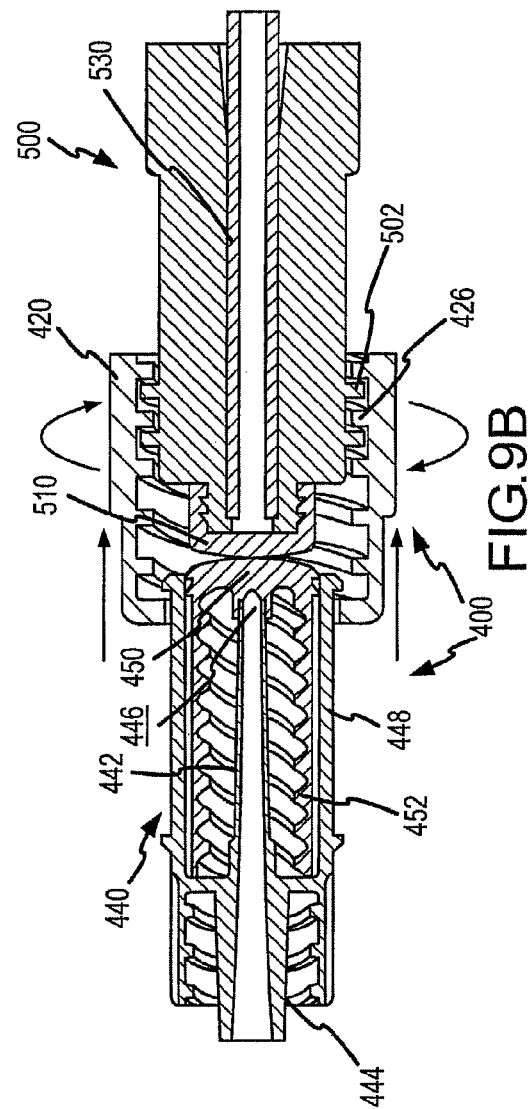

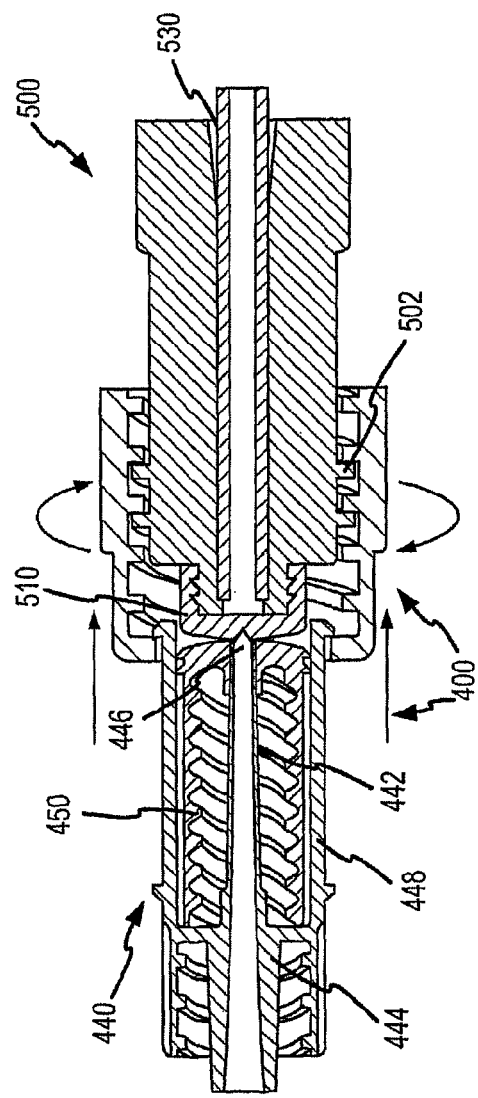
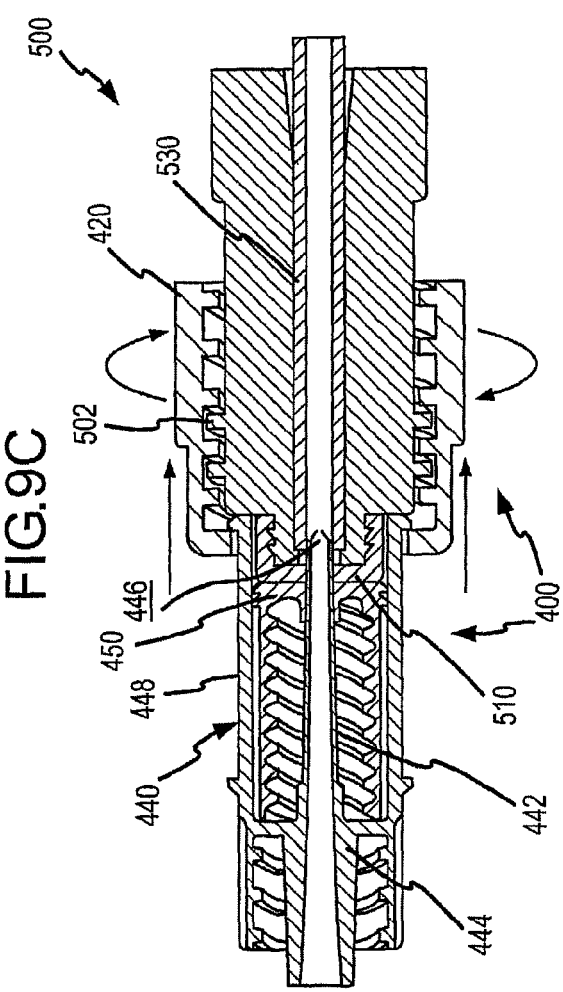
FIG.9C
FIG.9D

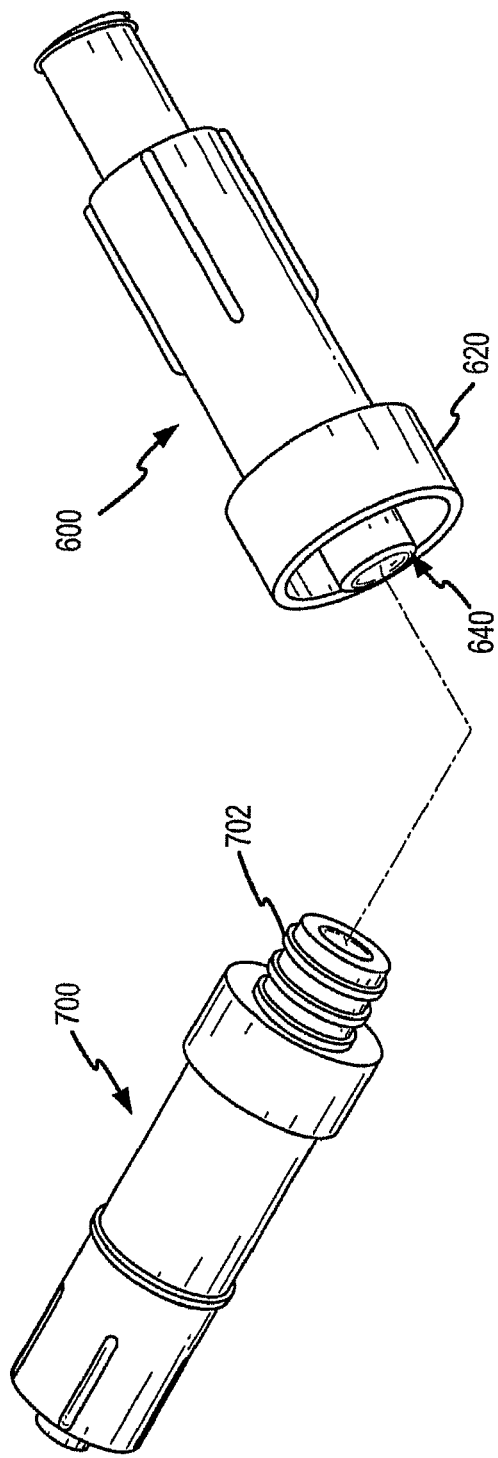
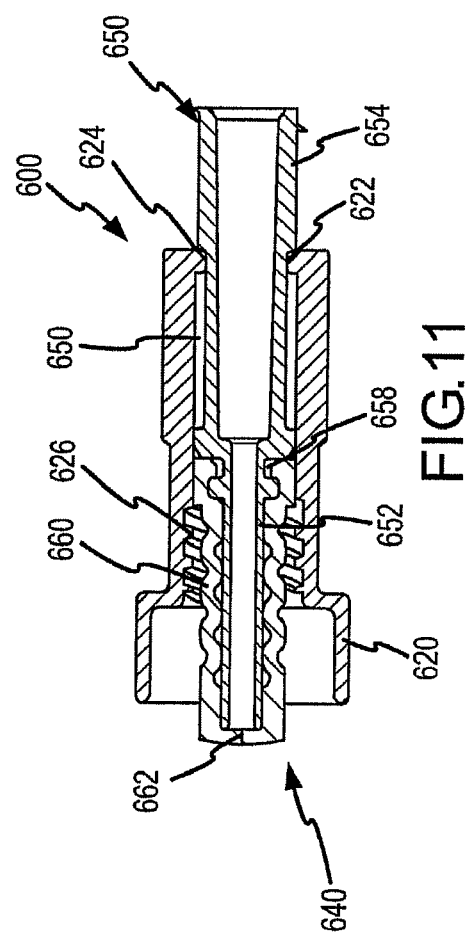

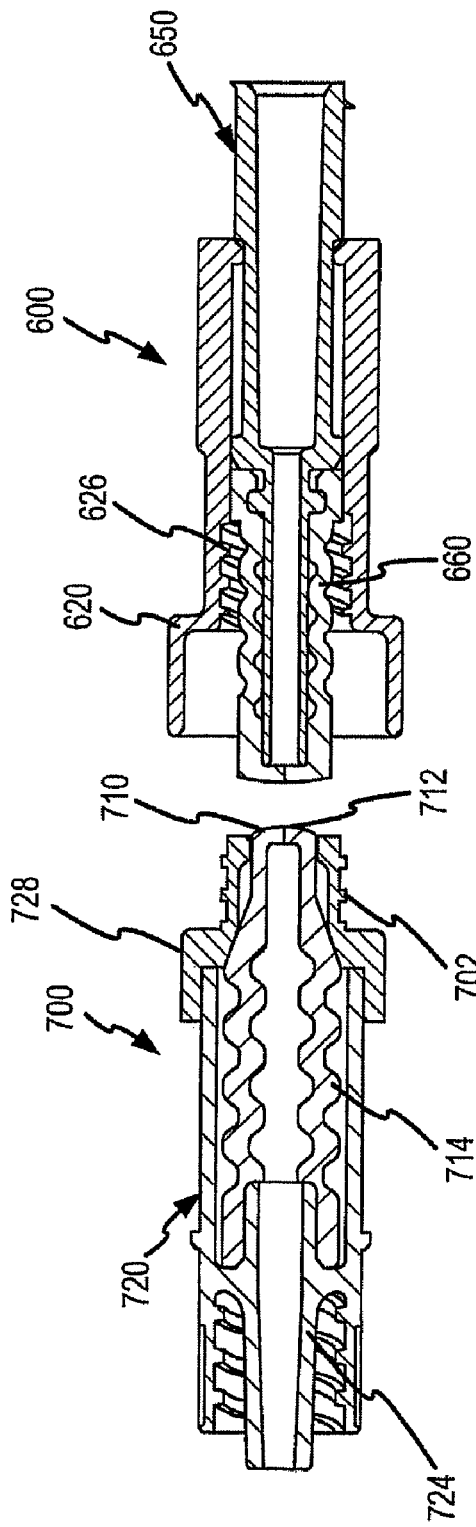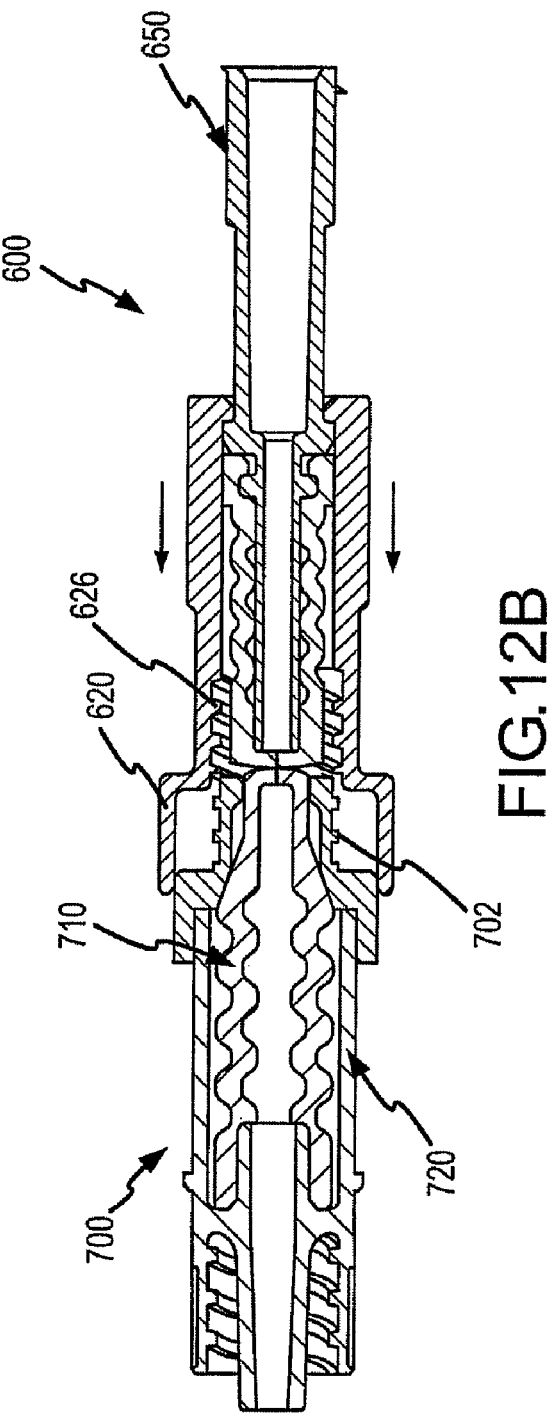
FIG.12A
FIG.12B

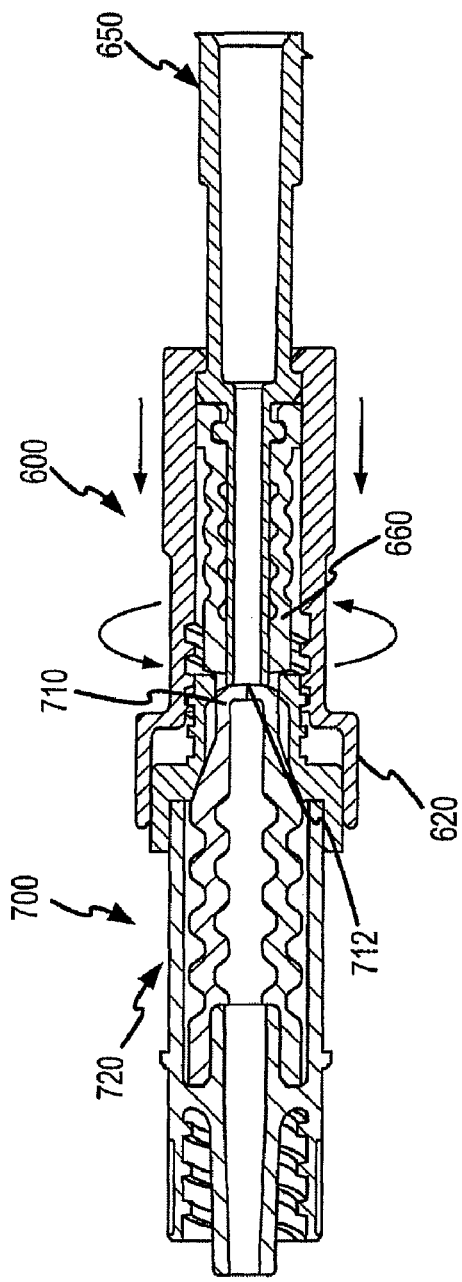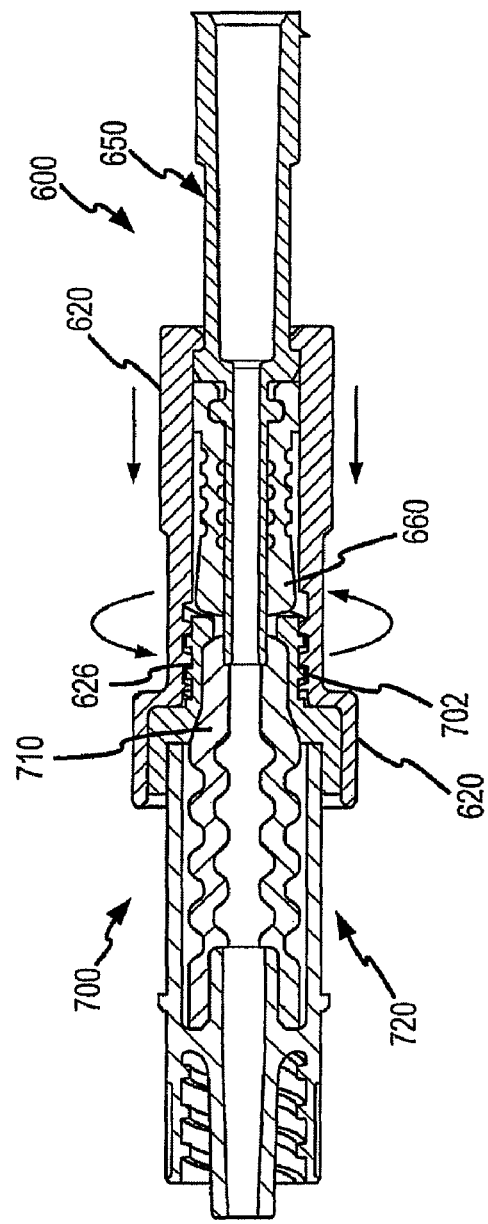

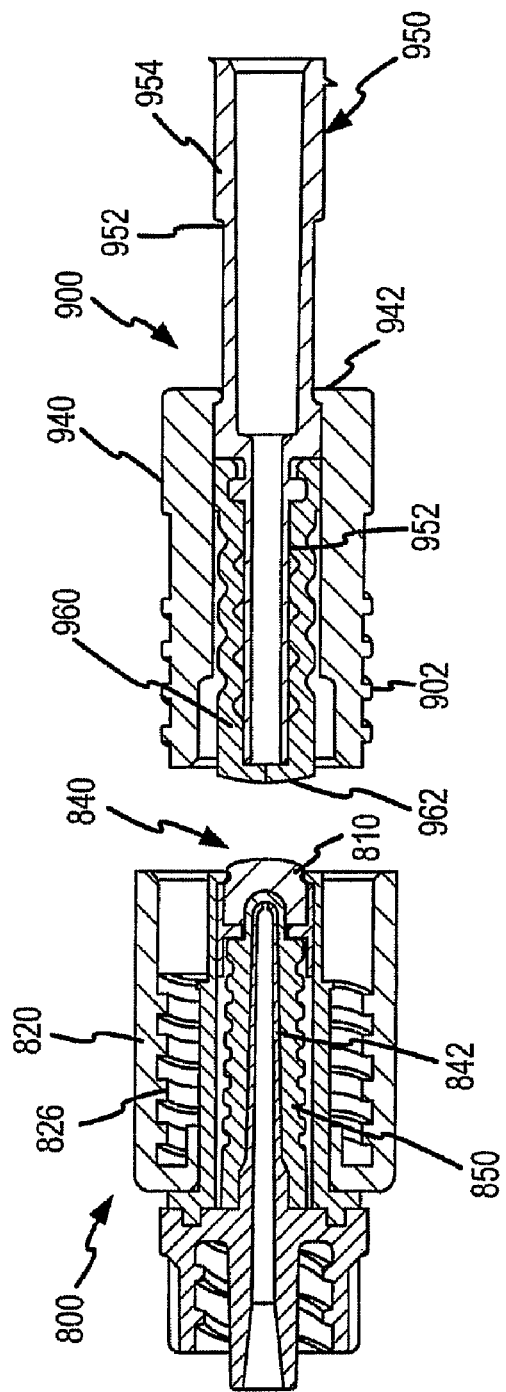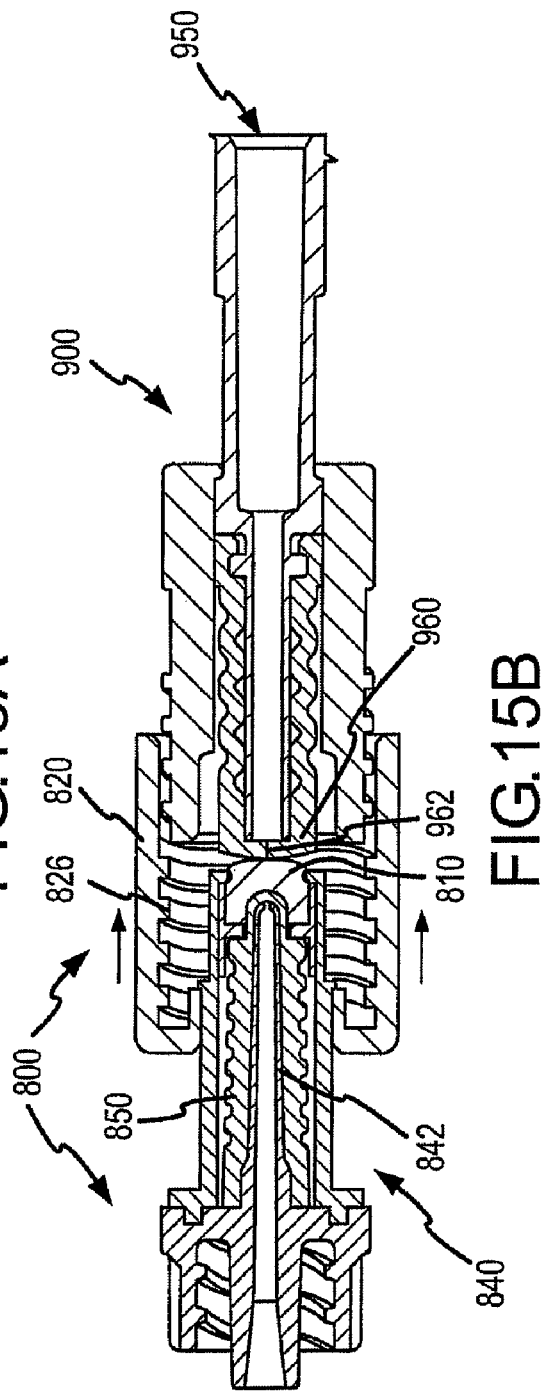
FIG.15A
FIG.15B

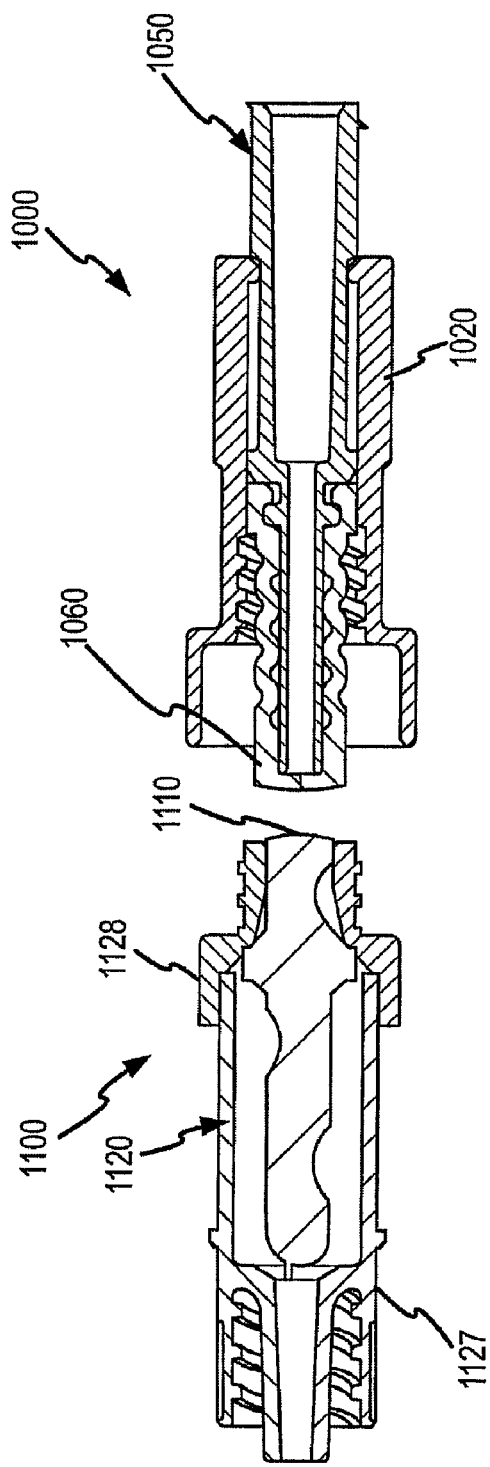
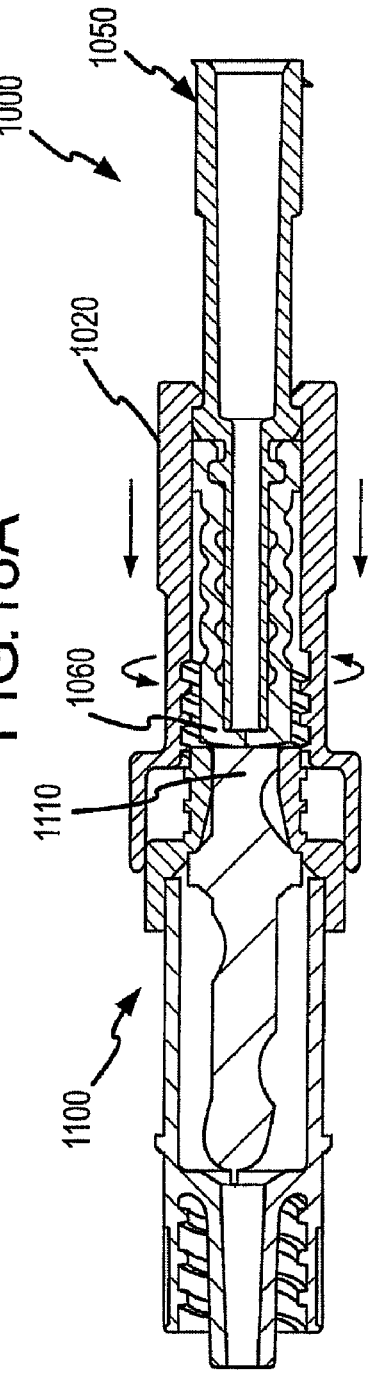
FIG.18A
FIG.18B

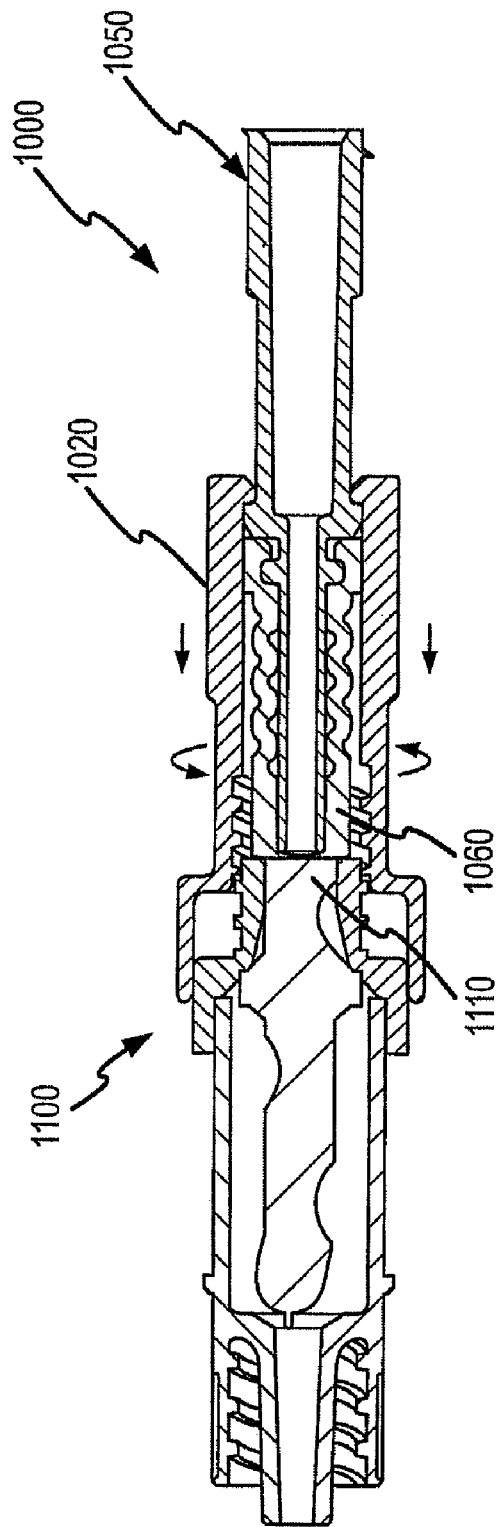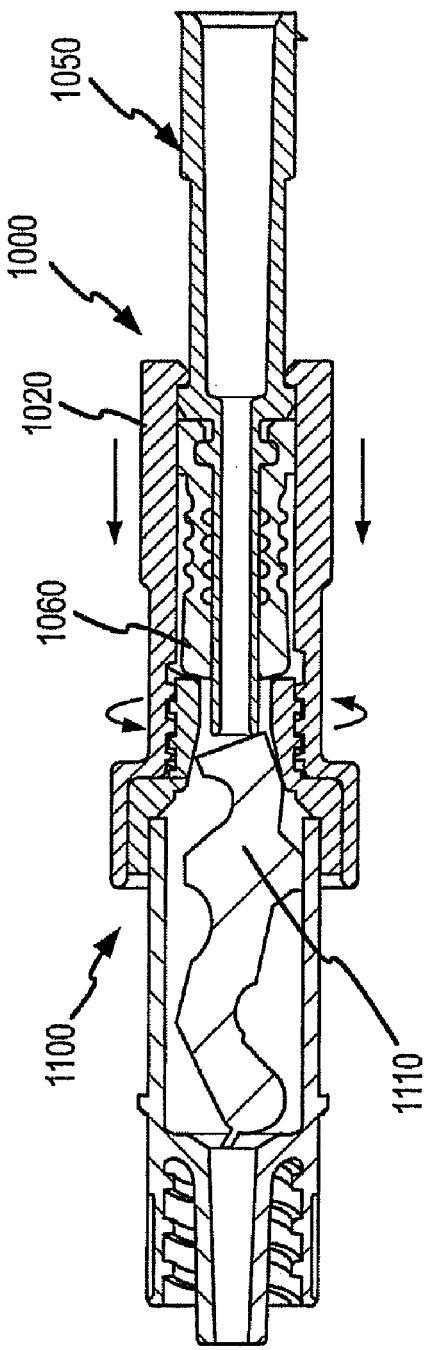
FIG.18C
FIG.18D

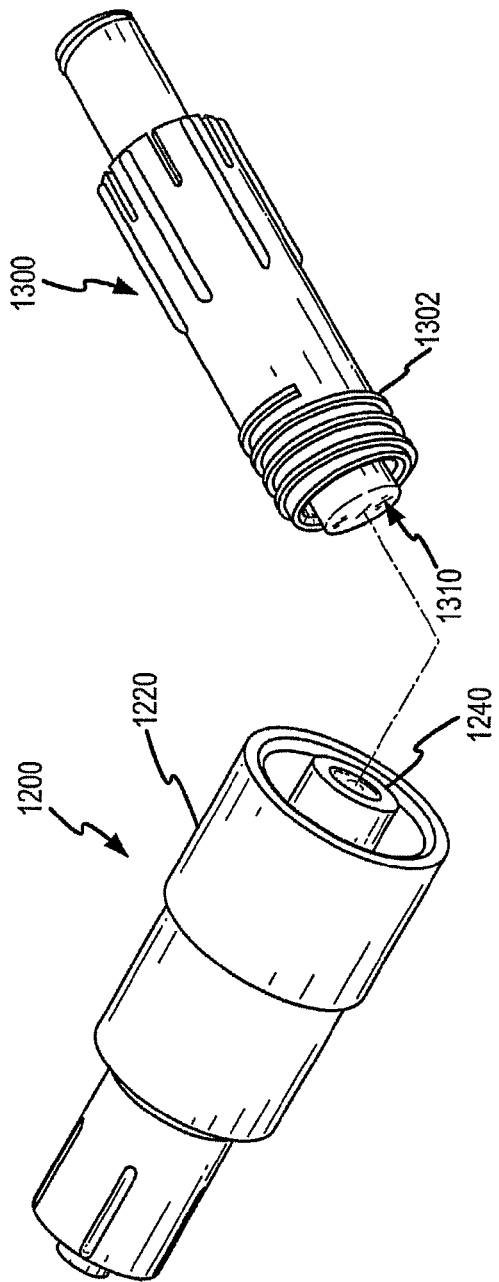
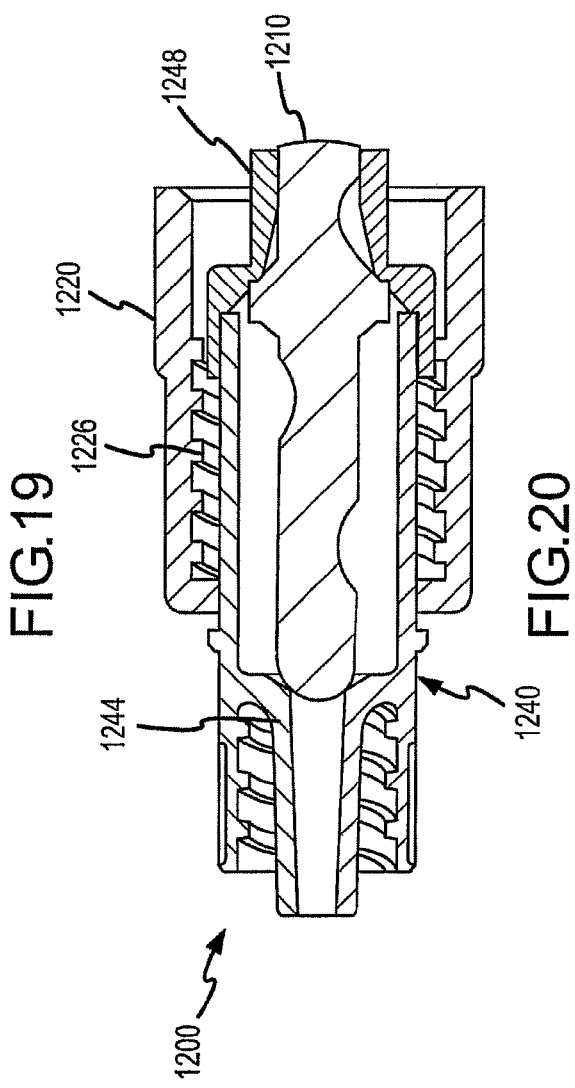

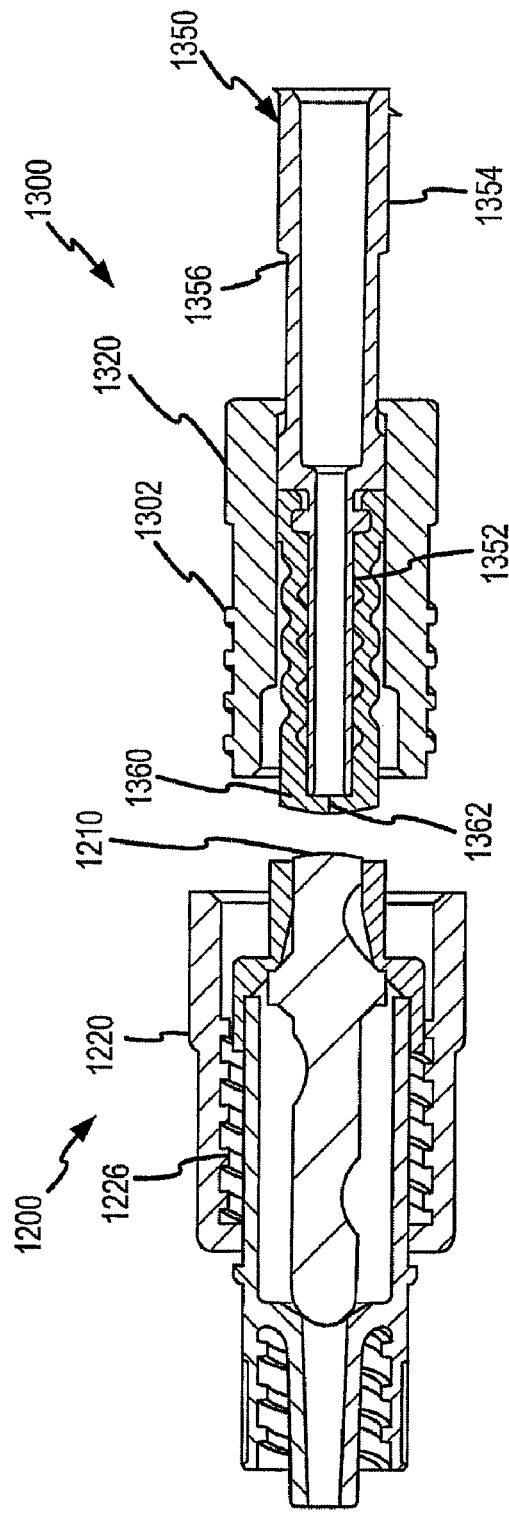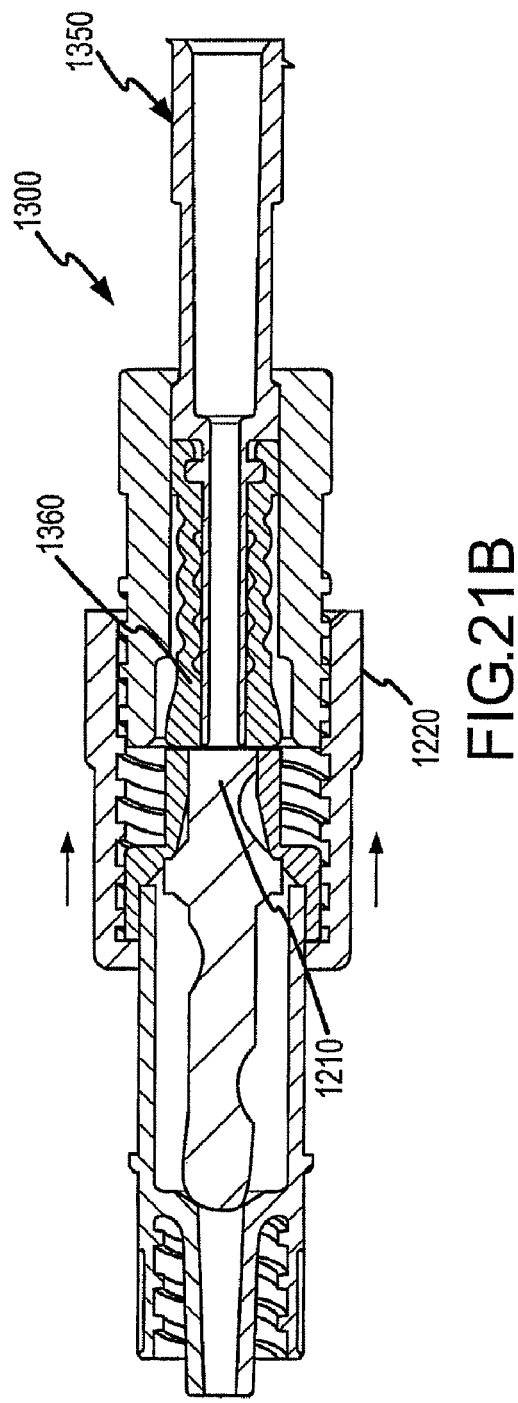
FIG.21A
FIG.21B

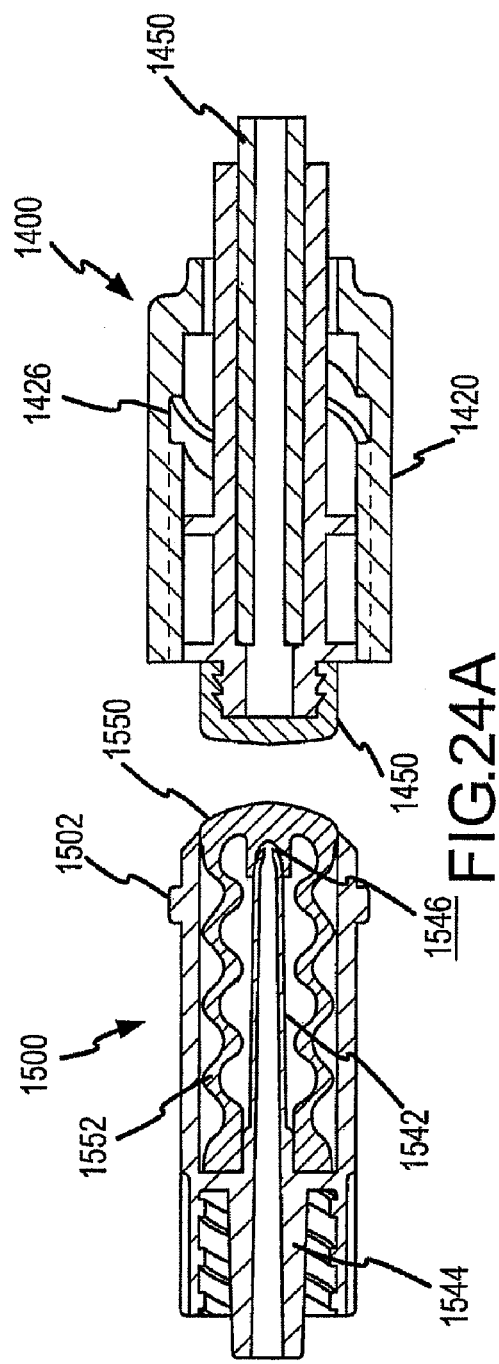
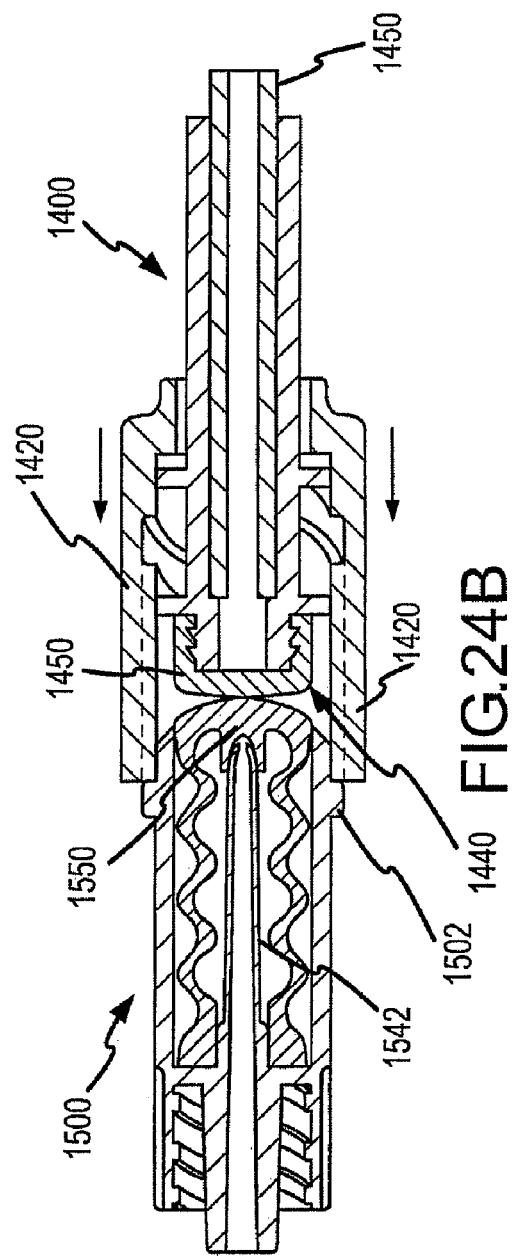

SWABABLE FLUID CONNECTORS AND FLUID CONNECTOR PAIRS

RELATED APPLICATIONS

This application is a continuation and claims priority to U.S. patent application Ser. No. 11/036,644, filed on Jan. 14, 2005, entitled "SWABABLE FLUID CONNECTORS AND FLUID CONNECTOR PAIRS," now U.S. Pat. No. 7,396,051, the entirety of which is hereby incorporated by reference.

FIELD OF THE INVENTION

The present invention relates to the field of fluid connectors, and more particularly, to fluid connectors that may be selectively interconnected to and disconnected from other fluid connectors for selective fluid transfer therebetween, wherein a distal end of an internal member of at least a first fluid connector may be readily accessed for sterilization, e.g. via an antibacterial swabbing operation, prior to interconnection with a second fluid connector. The inventive features are particularly apt for use in medical liquid transfer applications, including in particular male and female connectors employed in the administration of medical liquids to patients via intravascular catheters.

BACKGROUND OF THE INVENTION

Numerous techniques are employed for the administration of "medical liquids" (e.g. liquid medications and flush solutions) to a patient. In particular, where repeated medication infusions are required, medical liquids are often administered via the use of a vascular access catheter that is fluidly interconnected or interconnectable to one or more medical liquid sources. Typically, the catheter is inserted into the vein of a patient and left there for multiple intravenous (IV) infusions during an extended course of medication therapy. By way of example, the time period between IV drug infusions may be between about 4 to 24 hours.

In conjunction with extended therapy applications, a desirable practice is to disconnect a vascular catheter from a medical liquid source(s) between infusions. In this regard, most patients receiving IV medication therapy are ambulatory to some degree and benefit from not being continuously connected to a medical liquid source(s). To facilitate the ready and repeated connection/disconnection of a vascular catheter and medical liquid source(s), while avoiding the use of needle-type arrangements (e.g. arrangements where sharp/blunt needle ends are inserted into specialized vascular catheter connection ports having a pierceable/slit stopper), complimentary female and male fluid connectors are often utilized. For purposes hereof, a "male connector" generally refers to any fluid connector having a member that projects into a "female connector" upon interconnection therewith, wherein fluid transfer between the male and female connector may be realized.

In this regard, for example, a female connector may be fluidly interconnected as an access port to the vascular catheter and a complimentary male connector may be fluidly interconnected or readily interconnectable to a medical liquid source(s). In order to maintain sterility, various female connector designs have been employed that allow the female connector interconnection sites to be contacted with an antibacterial material (e.g. an alcohol solution) before each interconnection with a male connector. By way of example, U.S. Pat. Nos. 6,113,068, 6,706,022 and 5,782,816 are directed to female connectors having swabable interconnection sites.

To date, however, a largely unaddressed circumstance of infectious material introduction to the bloodstream of a patient is when a male connector is used for multiple interconnections. Known male connectors employed for repeated interconnections (e.g. to a female connector/vascular catheter arrangement) typically include a cylindrical port that is surrounded by an axially-fixed collar having internal threading that provides a means of securely connecting the male connector to a female connector that has external threading. Of note, such male connectors generally have inaccessible space between the axially-fixed collar and port. In turn, upon repeated usage of such male connectors, there are multiple opportunities for blood, nutritional fluids, and other fluids which include infectious materials to dwell in this space, and removal of such material and proper cleaning with antiseptic solutions is difficult to be effective.

SUMMARY OF THE INVENTION

In view of the foregoing, a primary objective of the present invention is to provide an improved fluid connector that facilitates cleaning (e.g. disinfecting) prior to initial and any repeated interconnection(s) with another fluid connector, thereby reducing the likelihood of introduction of undesired material into a fluid stream passing between the connectors.

A further objective of the present invention is to provide an improved male connector or female connector that may be easily cleaned and readily employed or otherwise adapted for use with a wide variety of female connector designs or male connector designs, respectively.

An additional objective of the present invention is to provide an improved fluid connector that is not only readily cleanable but also easy-to-use.

Yet a further objective of the present invention is to provide compatible fluid connector pairs (e.g., male and female connector pairs) that may be combinatively employed to reduce the likelihood of introduction of undesired material into a fluid stream passing between the connectors.

One or more of the above-noted objectives and additional advantages are realizable by an improved fluid connector of the present invention. The fluid connector includes an internal member and an outer collar supportably disposed about the internal member. A fluid passageway extends through at least a portion of the connector. Importantly, the outer collar is disposed for selective advancement and retraction relative to the internal member. For example, the outer collar may be slidably and/or rotatably advanced/retracted relative to the internal member. The ability to advance/retract the collar relative to the internal member facilitates cleaning of the connector prior to interconnection with another connector.

In one aspect, the outer collar and internal member are preferably disposed so that a distal end of the internal member is at least substantially flush with a distal end of the outer collar when the outer collar is in a retracted position relative thereto. In certain arrangements, a distal portion of the internal member (e.g. a distal end and adjoining sidewall portion) projects beyond a distal end of the outer collar when the outer collar is in a retracted position relative thereto. Such relative positioning optimally allows the distal end or distal portion of the internal member to be readily accessed by a user for cleaning prior to one or repeated interconnections with one or other fluid connectors. For example, a distal end or a distal portion of the internal member may contacted by a swab having a disinfectant applied thereto.

As may be appreciated, the noted cleaning capability yields an improved fluid connector that can be employed in a manner that reduces the risk of introduction of contaminates into a fluid stream to be passed between a pair of connectors during use. Such advantage is of particular merit in medical applications, including applications involving the administration of one or more medical liquid(s) to a patient via an intravascular catheter fluidly interconnected to one of the fluid connectors.

In another aspect of the inventive connector, the distal end or distal portion of the internal member of the inventive connector may be provided to be substantially closed or closeable when the connector is disconnected from another fluid connector. For example, the distal end or distal portion of the internal member may be provided so that it may present a substantially continuous surface that extends over the entirety of the distal end or distal portion when the inventive connector is disconnected from another fluid connector. As may be appreciated, the provision of a substantially closed or closeable, distal end or distal portion enhances the effectiveness of disinfectant swabbing.

In a related aspect, the fluid passageway of the inventive connector may be at least partially defined by a first passageway extending through at least a portion of the internal member. In this regard, a distal end of the first passageway may be defined to extend through an outer surface of the distal end or distal portion of the internal member, wherein the distal end of the first passageway is either closed or closeable when the inventive connector is disconnected from another fluid connector, and wherein the distal end of the first passageway is either opened or selectively openable when the inventive connector is interconnected with a another fluid connector.

In one approach, the internal member may comprise a first member having at least a distal portion of the first passageway extending therethrough, and a second member positioned about at least a distal portion thereof. In some embodiments utilizing this approach a distal end of the first member may be tubular and the second member may comprise a resilient material (e.g. an elastomeric material) that extends over the distal end of the first member to define a substantially closed, distal end or distal portion of the internal member. In certain arrangements, when mechanically interconnected with another fluid connector, the distal end of the first member may forcibly penetrate through the second member (e.g. the second member may comprise a slit or be piercable by the first member), wherein the tubular distal end of the first member sealably projects into a fluid passageway of the other fluid connector to establish a fluid interconnection therebetween. In other arrangements, when mechanically interconnected with another fluid connector, a tubular distal end of the other connector may forcibly penetrate through the second member (e.g. the second member may comprise a slit or be piercable), wherein the tubular distal end of the other connector sealably projects into the tubular end of the first member to establish a fluid interconnection therebetween.

In other embodiments utilizing an internal member comprising first and second members, the first and second members may be disposed for relative movement therebetween (e.g. relative slidable movement). In this regard, a closed, distal end of the first member may be provided to substantially fill an opening at a tubular distal end of the second member in a first relative position (e.g., to combinatively define a substantially closed, distal end or distal portion of the internal member). The first and second members may be selectively positionable to define an access to a first passageway extending through at least a portion of the first member in a second relative position. In one arrangement, to provide the passageway access the first member may be slidably moved from an advanced first position to a retracted second position relative to the second member. In such an arrangement, the first passageway may include an axial portion and a radial portion extending through an outer, side surface of the first member in a reduced distal portion thereof. In conjunction with mechanical interconnection to another connector the tubular distal end of the second member may sealably project into a fluid passageway of the other connector and the first member may be retracted from a first relative position to a second relative position, wherein fluid interconnection between the two connectors may be established.

In another approach, the internal member may comprise a resilient first member located within a distal end of a tubular second member. The distal end of the first member is substantially closed. In some embodiments utilizing this approach, the first member may be provided to be deflectable within the second member so as to define at least a distal portion of the first passageway through the tubular second member. When mechanically interconnected with another fluid connector, a tubular distal end of the other connector may depress and thereby deflect the first member, wherein the tubular distal end of the other connector sealably projects into the tubular second member to establish a fluid interconnection therebetween. In other embodiments, the first member may be provided to define at least a distal portion of the first passageway therethrough. When mechanically interconnected with another fluid connector, a tubular distal end of the other connector may forcibly penetrate through the distal end of the first member, wherein the tubular distal end of the other connector sealably projects into the distal portion of the first passageway defined by the first member to establish a fluid interconnection therebetween.

In another aspect of the inventive connector, the outer collar of the connector may include an interconnection surface for selective interconnection of the connector to another connector. For example, when the outer collar is rotatably disposed about the internal member, the interconnection surface may advantageously comprise a threaded surface, on an internal surface or external surface of the outer collar, for threadable engagement with a complimentary, threaded surface of another fluid connector. In some arrangements, the distal end of the interconnection surface may be aligned or proximally offset relative to a distal end of the internal member when the outer collar is in an advanced position relative thereto. Such arrangements accommodate the joint establishment of mechanical and fluid interconnections between two fluid connectors.

In other arrangements, a distal end of the interconnection surface may be distally offset relative to a distal end of the internal member when the outer collar is in an advanced position relative thereto. These arrangements facilitate easier mechanical interconnection of the inventive connector to another connector including. For example, the noted distal offset accommodates overlapped/underlapped interconnected positioning of the outer collar relative to a compatible fluid connector (e.g. via complimentary internal and external threaded surfaces or vice versa), without requiring forcible axial contact between the internal member of the inventive connector and the other fluid connector. Further the noted distal offset accommodates mechanical interconnection of the inventive connector to another fluid connector without requiring contemporaneous fluid interconnection therebetween.

By way of example, in fluid connector embodiments utilizing an internal member having a first member and a resilient second member disposed about a distal end of the first member, the connector may be provided so that upon advancement of the connector to a first interconnected position with another connector, (e.g. via rotational, threaded engagement therebetween), mechanical interconnection is realized free from fluid interconnection. Then, upon further relative advancement of the inventive connector to a second interconnected position, the first member forcibly penetrates through the second member to establish fluid interconnection with the other connector. Similarly, in fluid connector embodiments utilizing an internal member having a first member with a closed, distal end moveably disposed (e.g. slidably disposed) within an opening at a tubular distal end of a second member, the connector may be provided so that upon advancement of the connector to a first interconnected position with another connector (e.g. via rotational, threaded engagement), mechanical interconnection is realized free from fluid interconnection. Then, by moving (e.g. slidably retracting) the first member relative to the second member an access is provided to a passageway through the first member to yield fluid interconnection between the two connectors.

In another characterization of the present invention, inventive connector pairs adapted for selective interconnection and fluid transfer therebetween are provided. An inventive connector pair includes a first connector having an interconnection surface and a fluid passageway. A second connector may include an internal member and an outer collar supportably disposed about the internal member for selective advancement and retraction relative thereto. Preferably, the outer collar is disposed so that a distal end of the internal member is at least substantially flush when the outer collar is in a retracted position relative thereto. In some arrangements, a distal portion of the internal member (e.g. a distal end and adjoining sidewall portion) projects beyond a distal end of the outer collar when the outer collar is in a retracted position relative thereto. The second connector may further include a fluid passageway and interconnection surface adapted for mechanical interconnection with the interconnection surface of the first connector. As may be appreciated, in various aspects of the inventive connector pair, the second connector may comprise the various features of the inventive fluid connector described above.

In certain embodiments, the first and second connectors may be provided so contemporaneous with mechanical interconnection therebetween, the fluid passageway of the first connector and fluid passageway of the second connector are fluidly interconnected. In other embodiments, the first and second connectors may be provided so that, after mechanical interconnection of the connectors, the fluid passageways thereof may be selectively, fluidly interconnected by manipulation of one of the first and second connectors. For example, mechanical interconnection may be achieved via rotational, threaded engagement of the outer collar of the second connector with the first connector to a first interconnected position, and fluid interconnection may be achieved via further rotational, threaded engagement of the outer collar of the second connector with the first connector to a second position. In another approach, mechanical interconnection may be achieved via rotational, threaded engagement of the outer collar of the second connector with the first connector to an interconnected position, and fluid interconnection may be achieved via separate relative movement of first and second members comprising the internal member of the second connector.

In another aspect of an inventive connector pair, the first connector may include a resilient member disposed within or about an opening at a distal end of the first connector. In turn, the first and second connectors may be provided so that, upon mechanical interconnection between the first and second connectors, the resilient member is deflected or penetrated by the internal member of the second connector to establish a fluid interconnection therebetween. Further in this regard, the first connector may be provided so that a distal end of the fluid passageway thereof is substantially closed by the resilient member when the first connector is disconnected from the second connector. That is, a substantially closed distal end of the first connector may be provided, thereby facilitating cleaning.

In one approach, the first connector may include a tubular member having at least a portion of the fluid passageway defined therethrough. The tubular member may disposed for forcible advancement through the distal end of the depressible member of the first connector upon mechanical interconnection between the first connector and male connector. In another approach, the first connector may include a tubular member within which the depressible member is disposed, wherein at least a portion of the fluid passageway of the first connector is defined between the depressible member and the tubular member.

In yet another characterization of the present invention, inventive connector pairs are provided, wherein a first connector of each given pair comprises an outer tubular member and an internal member having a substantially closed or closeable distal end or distal portion when disconnected. Further, a second connector of each given pair includes an outer tubular member and a resilient member disposed about or within a distal opening of the tubular member. Of note, a distal end or distal portion of the resilient member is substantially closed or closeable when disconnected. The closed-end features of the first and second connectors comprising each pair advantageously yield a dual-swabable arrangement. Such arrangement is further enhanced via the inclusion of an advanceable/retractable collar in at least the first connector of each inventive connector pair.

As will be appreciated, an inventive method for handling at least a first fluid connector is also provided by the present invention. In particular, the method includes a step of retracting an outer collar of a first connector relative to an internal member of the connector. Preferably, upon such retraction a distal end of the internal member is at least substantially flush with a distal end of the outer collar. In certain arrangements, upon retraction of the internal member projects beyond distal end of the outer collar. The method may further include the step of cleaning the distal end or distal portion of the internal member when the outer collar is in the retracted position, e.g. by contacting a distal end or distal portion with a disinfectant. As may be appreciated, the retracting step may be completed by a first hand of the user and the contacting step may be conveniently completed by a second hand of a user, wherein the two steps may be completed separately or in a manner that is at least partially overlapping.

In one aspect, the inventive method may further include the steps of advancing the outer collar of the first connector relative to the internal member to an advanced position, e.g. utilizing a first hand of a user, and interconnecting the outer collar of the first connector to a second fluid connector with the outer collar in the advanced position, e.g. holding the first connector in a first hand and the second connector in a second hand of a user. In one approach, the interconnecting step may include the step of rotating the outer collar of the first connector relative to the other second connector. For example, the rotating step may include engaging an interconnection surface of the outer collar of the first connector (e.g. a threaded surface) with a complimentary interconnection surface of the second connector (e.g. a threaded surface).

In a related aspect, the inventive method may further include the step of establishing a fluid interconnection between the first connector and second connector either jointly with or separately from the step of interconnecting the outer collar of the first connector to the second connector. In either case, the establishing step may include the step of opening a first fluid passageway that extends through at least a portion of the internal member of the first connector.

In one approach, the internal member includes a first member having at least a portion of the first fluid passageway extending therethrough and a resilient second member disposed about a distal end of the first member, wherein the opening step may include a step of forcibly penetrating a distal end of the first member through the second member. In another approach, the internal member includes a first member with a closed, distal end moveably disposed (e.g. slidably disposed) within a distal, tubular end of a second member, wherein the opening step includes the step of moving (e.g. slidably retracting) the first member relative to the second member.

As may be appreciated, the inventive method may extended to the handling inventive fluid connector pairs, as will be further described above. In such arrangements, the distal ends of both connectors may be provided to be substantially closed when disconnected, thereby facilitating cleaning of each connector prior to interconnection.

Numerous additional aspects and advantages of the present invention will be recognized by those skilled in art upon consideration of the further description that follows. In conjunction with such description, it will also be realized that the various inventive features can be implemented in either male or female connectors.

BRIEF DESCRIPTION OF THE DRAWINGS

FIGS. 3A-3D are cross sectional views of the male connector embodiment and female connector of FIG. 1, shown in progressive stages of interconnection.

FIGS. 6A-6D are cross sectional views of the male connector embodiment and female connector of FIG. 4, shown in progressive stages of interconnection.

FIGS. 9A-9D are cross sectional views of the male connector embodiment and female connector of FIG. 7 shown in progressive stages of interconnection.

FIG. 10 illustrates opposing perspective views of another embodiment of an inventive male connector and a female connector interconnectable therewith.

FIG. 11 is a cross sectional view of the male connector embodiment of FIG. 10.

FIGS. 12A-12D are cross sectional views of the male connector embodiment and female connector of FIG. 10, shown in progressive stages of interconnection.

FIGS. 15A-15E are cross sectional views of the female connector embodiment and male connector of FIG. 13, shown in progressive stages of interconnection.

FIGS. 18A-18D are cross sectional views of the male connector embodiment and female connector of FIG. 16, shown in progressive stages of interconnection.

FIG. 19 illustrates opposing perspective views of another embodiment of an inventive female connector and a male connector interconnectable therewith.

FIG. 20 is a cross sectional view of the female connector embodiment of FIG. 19.

FIGS. 21A-21D are cross sectional views of the female connector embodiment and male connector of FIG. 19, shown in progressive stages of interconnection.

FIGS. 24A-24D are cross sectional views of the female connector embodiment and male connector of FIG. 22, shown in progressive stages of interconnection.

DETAILED DESCRIPTION OF THE INVENTION

Figure 1:
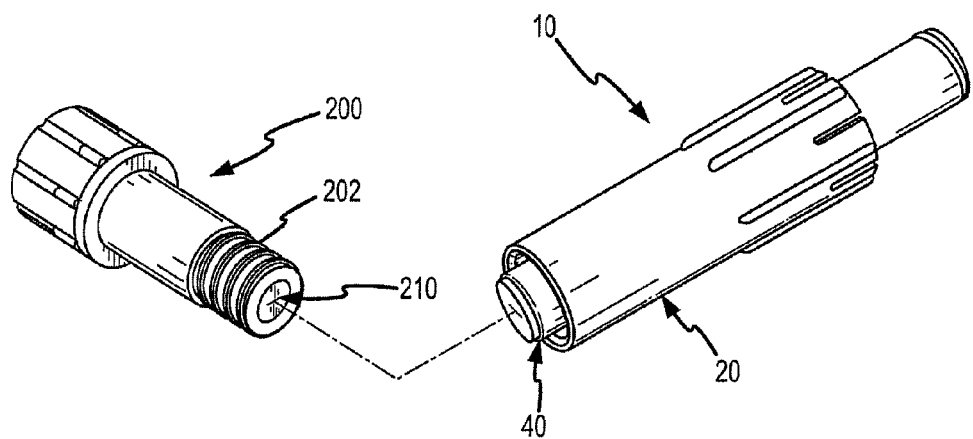
FIG. 1 illustrates opposing perspective views of one embodiment of an inventive male connector and a female connector interconnectable therewith.
Figure 2:
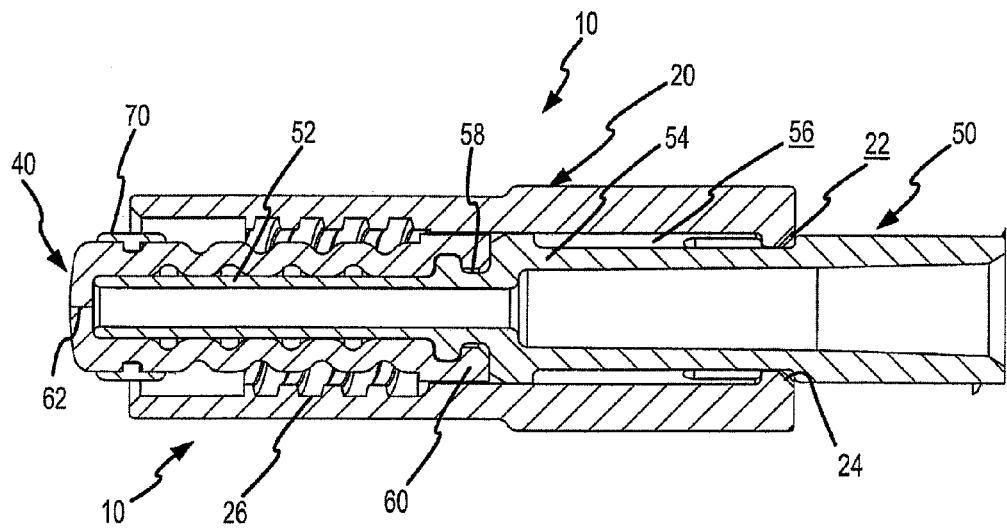
FIG. 2 is a cross sectional view of the male connector embodiment of FIG. 1.

FIGS. 1 and 2 illustrate one embodiment of a fluid connector comprising the present invention. In this embodiment, a male connector 10 is provided for selective interconnection and fluid transfer with a female connector 200, e.g., a female connector as described in U.S. Pat. No. 6,113,068 hereby incorporated by reference in its entirety.

Before proceeding, it should be noted that fluid connectors of the present invention may include male and/or female connector implementations. Further, such implementations may be readily adapted for use with a wide variety of known fluid connector types, including in particular fluid connectors utilized in medical applications involving the transfer of medical liquids. In such various adaptations, fluid connectors of the present invention facilitate cleaning by a user (e.g. the application of a disinfectant) prior to interconnection with another fluid connector.

In the embodiment shown in FIG. 1, such capability may be provided by male connector 10 via the employment of an outer collar 20 that is supportably disposed about and interconnected with an internal member 40 for selective advancement and retraction relative thereto. For example, outer collar 20 may be slidably and rotatably disposed about internal member 40. In FIG. 1, the outer collar 20 is shown in a retracted position so that a substantially closed, distal portion of the internal member 40 is exposed. In this position, the distal portion of internal member 40 may be readily contacted with a disinfectant. For example, a distal end and adjoining sidewall portion of the internal member 40 may be advantageously contacted by a fabric swab having a disinfectant applied thereto. As will be appreciated, female connector 200 may also present a substantially closed, distal end that may be readily swabbed with a disinfectant prior to interconnection with the male connector 10.

Referring to FIG. 2, internal member 40 may comprise a tubular main body 50, a resilient, closed-end sheath 60 positioned about a distal portion 52 of the main body 50, and a ring member 70 located about the resilient sheath 60. The main body 50 may further include an enlarged proximal portion 54, wherein the proximal portion 54 extends through an opening 22 at a proximal end of the outer collar 20. The proximal portion 54 of main body 50 may be provided with an annular recess 56 that extends about and along the proximal portion 54 of the main body 50. The proximal portion 54, recess 56 and outer collar 20 may be sized so that a proximal end flange 24 of the outer collar 20 may travel along the recess 56 as outer collar 20 is advanced and retracted relative to internal member 40. As shown, the proximal end flange 24 may also serve to co-axially align the outer collar 20 and internal member 40, and to restrict the relative range of advancement/retraction to the length of the recess 56.

A proximal end of resilient sheath 60 is restrainably engaged within an annular groove 58 of the main body 50 (e.g. utilizing hoop strength at the proximal end of sheath 60 and/or by bonding and/or by capture between main body 50 and outer collar 20). Resilient sheath 60 may also include sidewall undulations so as to resiliently bias the resilient sheath 60 to the position shown in FIG. 2. A slit 62 may extend through the closed, distal end of the resilient sheath 60, wherein a distal end of the main body 50 may forcibly penetrate through the slit 62 at the distal end of the resilient sheath 60. As will be further described, upon advancement of the distal end of main body 50 through slit 62 at the distal end of resilient sheath 60 a fluid passageway extending through main body 50 may be accessed for medical liquid transfer to/from the female connector 200 upon interconnection therewith. Upon retraction of the distal end of main body 50 through the slit 62 of resilient sheath 60, ring member 70 may act to facilitate the closure of the distal end of resilient sheath 60 at slit 62. In this regard, the resilient nature of resilient sheath 60 may provide the spring force for closure.

In medical applications, the proximal end 54 of main body 50 may be interconnected (e.g. bonded) to a tubing line that is fluidly interconnected or interconnectable with one or more sources medical liquid (e.g. liquid medication, saline solution, etc.) or with an intravascular catheter. In other arrangements, the proximal end 54 of main body 50 may be provided with a coupling member (e.g. a female luer connector) for selective interconnection with a compatible coupling member (e.g. a rotatable male luer) disposed at an end of a tubing line that is connected or connectable to one or more a medical liquids source(s) or to an intravascular catheter.

The outer collar 20 of male connector 10 is provided with an interconnection surface 26 for selective interconnection of the male connector 10 with female connector 200. More particularly, the interconnection surface 26 may be internally located and may comprise a threaded surface that is sized/shaped for threadably engaging a complimentary-threaded, external surface 202 on female connector 200, as shown in FIG. 1.

Referring now to FIGS. 3A-3D, the use and interconnection of male connector 10 to female connector 200 will be described in detail. Initially, and as shown in FIG. 3A, outer collar 20 may be located in a retracted position relative to internal member 40 (e.g. via a manual, one-hand operation by a user), thereby exposing a distal end portion of internal member 40 for application of a disinfectant thereto (e.g. via a manual, other-hand operation by the user). Similarly, disinfectant may be applied to a distal end of a resilient member 210 located within an opening at a distal end of a tubular member 220 comprising female connector 200 (e.g. via a manual, two-handed operation by the user).

As shown in FIG. 3A, female connector 200 may include a tubular shank member 242 fixedly interconnected to tubular member 220 via a base member 244. For example, shank member 242 and base member 244 may be integrally formed with a fluid passageway extending therethrough, and tubular member 220 may be secured to base member 244. Base member 244 may be further provided with a proximal, tubular end portion having an internally threaded surface for selective interconnection with another connector (e.g. a threaded male connector provided at an end of a tubing line that is interconnected or interconnectable with an intravascular catheter or one or more medical liquid source(s)). An opening 246 may be provided at a distal end of shank member 242, and a resilient sheath 250 may be disposed about the shank member 242 and operatively interfaced with resilient member 210 via intermediate member 270. Resilient sheath 250 and/or resilient member 210 may be slit (e.g. pre-pierced) or pierceable at their distal ends to allow the distal end of shank member 242 to forcibly penetrate therethrough when interconnected to male connector 10. Resilient sheath 250 is provided to apply a spring-loading force to resilient member 210 via intermediate member 270, wherein resilient member 210 is maintained in the position shown in FIG. 3A (i.e. resilient member 210 substantially fills the distal end opening of female connector 200) when not interconnected to male connector 10. In this regard, resilient sheath 250 includes undulations 252, wherein the resilient sheath 250 is depressible in an accordion-like manner.

FIGS. 3B-3D illustrate the progression of interconnection of male connector 10 to female connector 200. In FIG. 3B outer collar 10 has been advanced relative to internal member 40 and threadably rotated to an initial interconnection position relative to female connector 200. In the position shown in FIG. 3B, the distal end of internal member 40 has just contacted the distal end of resilient member 210. Of note, such an initial interconnection position may be achieved without the need to overcome any spring-loading force. Further, it may be noted that in the position shown in FIG. 3B, the male connector 10 and female connector 200 may be advantageously mechanically interconnected without the establishment of a fluid interconnection therebetween. Such advantages may be realized in the illustrated arrangement due to the distally offset location of the distal end of the interconnection surface 26 relative to the distal end of the internal member 40 when outer collar 20 is in an advanced position. In other modified arrangements the distal end of interconnection surface 26 may be located so as to be aligned or proximally offset relative to the distal end of internal member 40 when the outer collar 20 is in an advanced position. As will be appreciated, such modified arrangements may provide for the contemporaneous establishment of mechanical and fluid interconnections between the modified male connector and a female connector.

In FIG. 3C, outer collar 20 has been rotatably advanced further onto female connector 200 to an advanced interconnection position relative to FIG. 3B (e.g. by a user holding female connector 20 with one hand and rotatably advancing the outer collar 20 with another hand), thereby causing the distal end of internal member 40 to depress resilient member 210 inwardly within female connector 10 against the spring-loading force applied by resilient sheath 250. Further, the distal end of main body 50 is shown forcibly-penetrated into slit 62 of flexible sheath 60, and the distal end of shank member 242 is shown forcibly-penetrated into slit 212 of resilient member 210. Each of the above-noted forcible penetration actions are advantageously achieved jointly with the rotatable, threaded advancement of outer collar 20 of male connector 10 relative to female connector 200.

FIG. 3D illustrates male connector 10 in a further interconnected position on female connector 200. That is, outer collar 20 has been rotatably advanced to a further advanced location relative to that shown in FIG. 3C, wherein the distal end of the tubular main body 50 of the internal member 40 has sealably engaged the spring-loaded resilient member 210, and wherein the distal end of shank member 242 is located within the distal end of tubular main body 50 of the internal member 40 to establish a fluid interconnection between the male connector 10 and female connector 200. In this regard, the shank member 242 may be tapered and sized relative to the distal end of tubular main body 50 to facilitate the establishment of a fluid interconnection therebetween. As will be appreciated, in this position fluid transfer between male connector 10 and female connector 200 may be carried out.

For example, a liquid medication may be administered to a patient via the male connector 10, female connector 200 and an intravascular catheter interconnected thereto, followed by a saline flush solution administered therethrough. Thereafter, the male connector 10 and female connector 200 may be disconnected by rotation of the outer collar 20 relative to the female connector 200. Subsequently, if further administration of medical liquid is desired utilizing male connector 10 and/or female connector 20, the male connector 10 and/or female connector 20 may be disinfected and reconnected to a female connector 200 as described above in relation to FIGS. 3A-3D.

Figure 4:
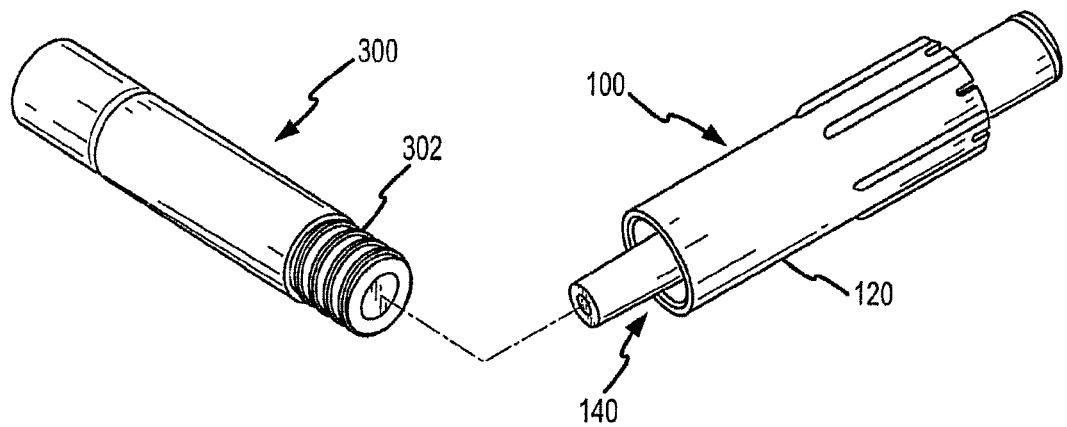
FIG. 4 illustrates opposing perspective views of another embodiment of an inventive male connector and another female connector interconnectable therewith.
Figure 5:
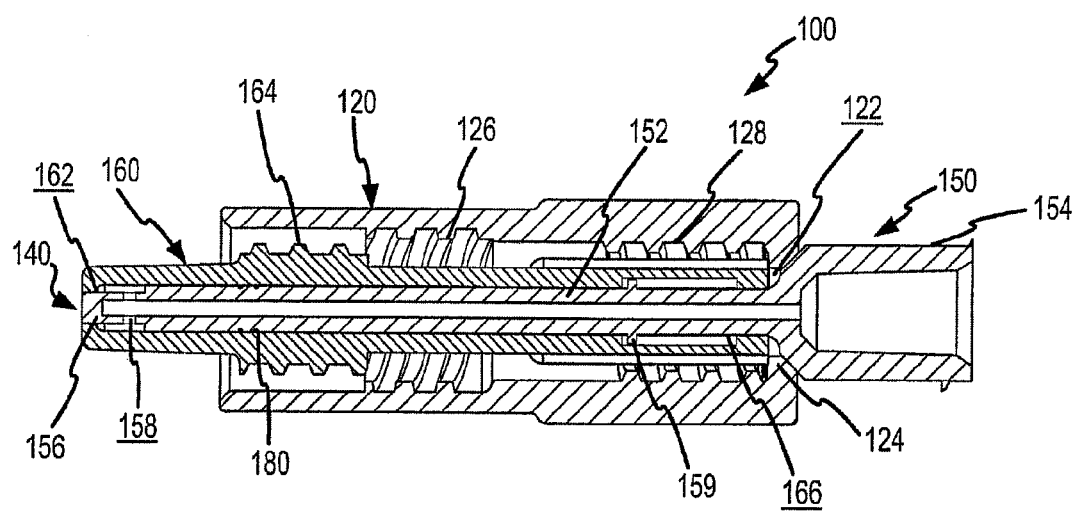
FIG. 5 is a cross sectional view of the male connector embodiment of FIG. 4.

FIGS. 4 and 5 illustrate another embodiment of an inventive male connector 100 adapted for selective interconnection with and fluid transfer between another type of a female connector 300, e.g. a female connector as described in U.S. Pat. No. 5,782,816, hereby incorporated by reference in its entirety. As shown in FIG. 4, male connector 100 includes an outer collar 120 that is supportably disposed about and interconnected with an internal member 140 for selective advancement and retraction relative thereto. For example, outer collar 120 may be slidably and rotatably disposed about internal member 140. In FIG. 4, the outer collar 120 is shown in a retracted position so that a substantially closed, distal portion of the internal member 140 is exposed. In this position, the closed, distal portion of internal member 140 may be disinfected or otherwise cleaned. For example, the distal end and adjoining sidewall portion of internal member 140 may be advantageously contacted by a fabric swab having a disinfectant applied thereto. As shown, the female connector 300 may also present a substantially closed, distal end that may be swabbed with a disinfectant prior to interconnection with male connector 100.

Referring to FIG. 5, internal member 140 may comprise a tubular main body 150 having a closed, distal end, a semi-rigid, tubular sheath 160 positioned about a reduced distal portion 152 of the main body 150, and optional sealing members 180 located about the distal portion 152 of main body 150. In addition to the reduced distal portion 152, the main body 150 may also include an enlarged proximal portion 154, wherein the proximal portion 154 is located outside of an opening 122 at a proximal end of the outer collar 120. The distal portion 152 of main body 150 and tubular sheath 160 may be sized so as to permit sliding advancement/retraction of the distal portion 152 within the tubular sheath 160, wherein the closed, distal end of tubular main body 150 substantially fills an opening 162 at the distal end of tubular sheath 160 when the main body 150 is located in an advanced position relative to the tubular sheath 160, thereby selectively yielding an internal member 140 having a substantially closed, distal end.

A stepped-in or reduced portion 156 may be provided near the distal end of main body 150 with one or a plurality of radial passageways 158 extending from an internal passageway of tubular main body 150 to an outer surface of the stepped-in portion 156. As will be further described, upon retraction of the main body 150 relative to tubular sheath 160, access to the fluid passageways extending through internal member 140 may provide for fluid transfer to/from female connector 300 upon interconnection therewith. In this regard, the proximal end 154 of main body 150 may be interconnected (e.g. bonded) with a tubing line that is fluidly interconnected with one or more fluid sources, (e.g. medical liquids) or an intravascular catheter.

In order to restrict main body 150 from being removable (e.g. withdrawn) from tubular sheath 160, an outer annular flange 159 may be provided on the main body 150 and a complimentarily annular recess 166 may be provided in opposing relation on tubular sheath 160 to receive the annular flange 159. As may be appreciated, the axial length of recess 166 accommodates a corresponding range of slidable advancement/retraction of main body 150 relative to tubular sheath 160, and the proximal end wall of recess 166 restricts main body 150 from withdrawal from tubular sheath 160. While not shown, it may also be preferable to provide a spring-loading member to bias main body 150 into an advanced position relative to tubular sheath 160 (e.g. a spring member may be interconnected to and extend between a proximal end of tubular sheath 160 and proximal end 154 of main body 150).

The outer collar 120 is provided with a first internal interconnection surface 126 for selective interconnection of the male connector 100 to female connector 300. More particularly, the internal interconnection surface 126 may comprise a threaded surface that is sized/shaped for threadably engaging an interconnection surface 302 of female connector 300, (e.g. a complimentary threaded surface 302 on the outside surface of female connector 300 as shown in FIG. 4). Further, the outer collar 120 may be provided with a second internal interconnection surface 128 for selective interconnection with a complimentary external interconnection surface 164 provided on tubular sheath 160. Specifically, and as shown in FIG. 5, the second internal interconnection surface 128 and external interconnection surface 164 may comprise complimentary, threaded surfaces sized/shaped for threadable engagement.

In this regard, and referring now to FIGS. 6A-6D, interconnection of male connector 100 to female connector 300 will be described in further detail. Initially, and as shown in FIG. 5A, the collar 120 may be located in a retracted position relative to internal member 140, and the main body 150 may be located in an advanced position relative to tubular sheath 160, wherein a substantially closed, distal end portion of internal member 140 is exposed for application of a disinfectant thereto. Also, disinfectant may be applied to a closed, distal end of a resilient member 310 located within an opening at a distal end of a tubular member 320 comprising female connector 300.

As shown in FIG. 6A, the resilient member 310 of the female connector 300 may be interconnected at a proximal end to the tubular member 320. For example, the resilient member 310 may be interconnected at a proximal end to a base member 324 that is rigidly interconnected to the tubular member 320. Further, resilient member 310 and tubular member 320 may be shaped so that resilient member 310 is captured within tubular member 320. As illustrated, a passageway extends from the proximal end of base member 324 through the tubular member 320. Of further note, the resilient member 310 may be sized/shaped relative to the tubular member 320 so that a portion of the resilient member 310 may be deflected within the tubular member 320 in response to being depressed at a distal end thereof. In other embodiments, the resilient member 310 may comprise a compressible material that compresses upon the application of a force applied to a distal end thereof. In any case, the resilient member 310 is of a resilient nature so that the distal end thereof is maintained in the position shown in FIG. 6A when the female member 300 is not interconnected to male connector 100 (e.g. the distal end of resilient member 310 substantially fills and thereby presents a substantially closed distal end within tubular member 320).

FIGS. 6B-6D illustrate the progression of interconnection of male connector 100 to female connector 300. In FIG. 6B, outer collar 120 has been advanced relative to internal member 140 and threadably rotated into threadable engagement with female connector 300. In the position shown in FIG. 6B, the substantially closed, distal end of internal member 140 has just contacted the distal end of resilient member 310. Of note, such interconnection may be achieved without the need to overcome any spring-loading. Further, it may be noted that in the position shown in FIG. 6B, the male connector 100 and female connector 300 may be advantageously mechanically interconnected without the establishment of a fluid interconnection therebetween.

In FIG. 6C, internal member 140 is shown in an advanced position relative to FIG. 6B, wherein the substantially closed, distal end of internal member 140 has begun to depress resilient member 310 inwardly within female connector 300. Such advancement is achieved by the rotational advancement of internal member 140 relative to outer collar 120. Specifically, the external interconnection surface 164 of tubular sheath 160 has been threadably advanced relative to the internal interconnection surface 128 of the outer collar 120. To achieve such advancement, a user may grasp outer collar 120 with one hand while rotating sheath 160 with the other hand. In the later regard, outer fins 168 or other surface contouring may be provided at a proximal end of tubular sheath 160 to facilitate manual rotation.

FIG. 6D illustrates internal member 140 in a further-advanced position relative to FIG. 6C, wherein the distal end of internal member 140 has further depressed the resilient member 310 into tubular member 320, thereby causing the resilient member 310 to deflect within the tubular member 320. Such advancement is achieved by further rotation of tubular sheath 160 relative to outer collar 120. Of further note, the sidewall surface along a distal portion of tubular sheath 160 has sealably engaged the inner periphery of the distal opening of tubular member 320. To facilitate such engagement, the distal portion of tubular sheath 160 may be tapered and/or may comprise a semi-rigid material.

As further shown in FIG. 6D, the main body 150 has been separately, slidably retracted relative to tubular sheath 160, thereby providing access to a fluid passageway that extends from the proximal end to the distal end of internal member 140. More particularly, the fluid passageway extends through opening 162 of tubular sheath 160, between the tubular sheath 160 and stepped-in portion 156 of main body 150, and through radial passageways 158 into the internal passageway of tubular main body 150. Due to the deflection of resilient member 310, the fluid passageway of internal member 140 is now in fluid communication with a fluid passageway extending through female connector 300 as shown.

In this position, fluid transfer between male connector 100 and female connector 200 may be carried out. For example, in a medical application a liquid medication may be administered to a patient via the male connector 100, female connector 300 and an intravascular catheter interconnected thereto, followed by a saline flush solution administered therethrough. Thereafter, the male connector 100 and female connector 300 may be disconnected by rotation of outer collar 120 relative to the female connector 300. Preferably, internal member 140 is also rotatably retracted relative to outer collar 120. Further main body 150 is preferably returned to an advanced position relative to tubular sheath 160 (e.g. either manually or via a spring-loading member), wherein the distal end of main body 150 is again located in the opening 162 of the tubular sheath 160 to present a substantially, closed distal portion on internal member 140. Subsequently, if a further administration of medical liquid is desired utilizing male connector 100 and/or female connector 300, the male connector 100 and/or female connector 300 may be disinfected via a swabbing operation and reconnected as described above in relation to FIGS. 6A-6D.

As may be appreciated, in certain applications it may be preferable to initially, rotatably advance tubular sheath 160 relative to outer collar 120. Following such advancement, male connector 100 may then be rotatably interconnected to female connector 300, wherein the distal end of internal member 140 will depress the distal end of depressible member 310 of the female connector 300 into the position as shown in FIG. 6D.

Figure 7:
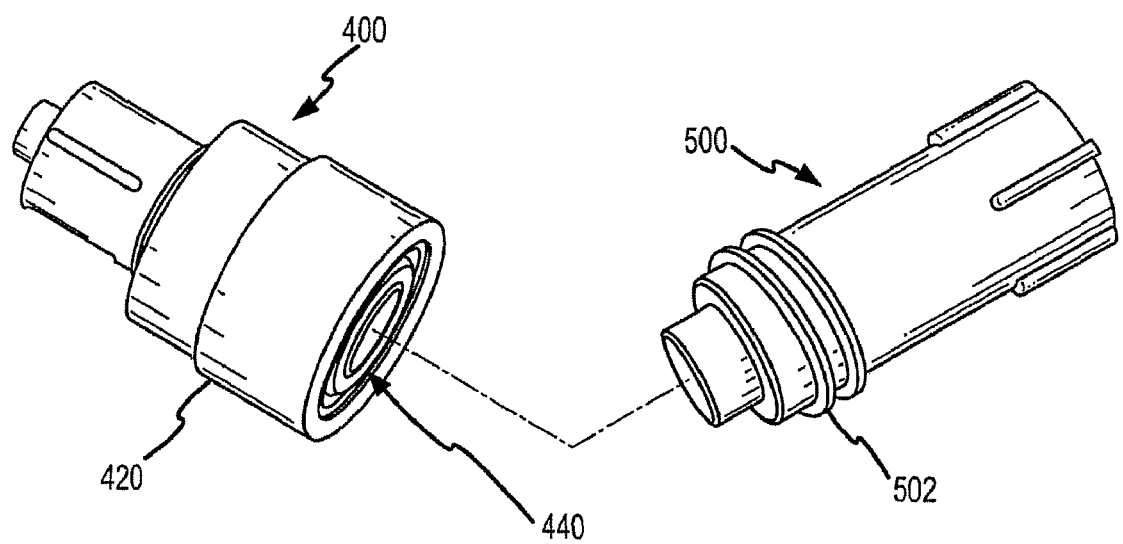
FIG. 7 illustrates opposing perspective views of one embodiment of an inventive female connector and a male connector interconnectable therewith.
Figure 8:
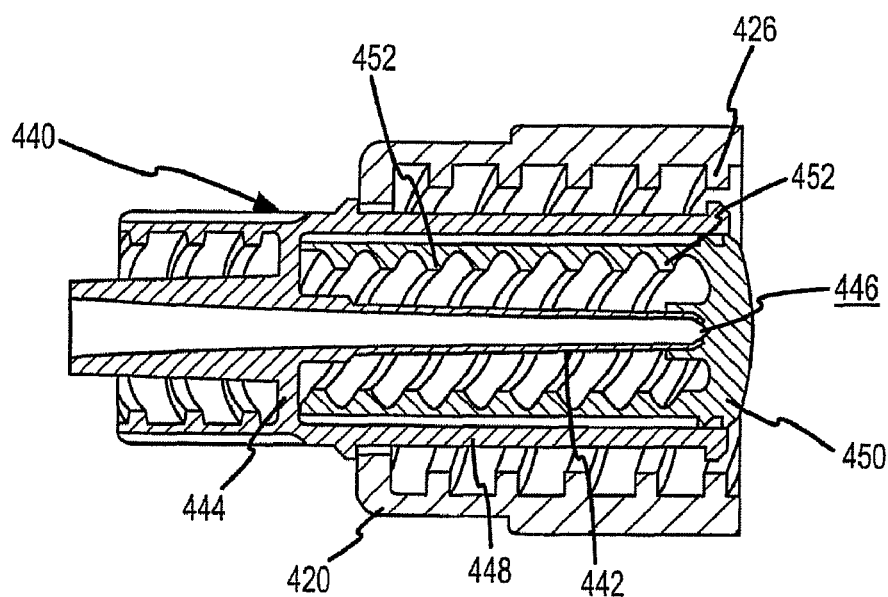
FIG. 8 is a cross sectional view of the female connector embodiment of FIG. 7.

FIGS. 7 and 8 illustrate an embodiment of a female connector 400 adapted for selective interconnection and fluid transfer with a male connector 500. As shown in FIG. 8, female connector 400 includes an outer collar 420 that is supportably disposed about and interconnected with an internal member 440 for selective advancement and retraction relative thereto. For example, outer collar 420 may be slidably and rotatably disposed about internal member 440. In FIGS. 7 and 8 the outer collar 420 is shown in a retracted position so that a substantially closed, distal end of the internal member 440 is readily accessible. In this position, the closed, distal end of internal member 440 may be disinfected or otherwise cleaned. For example, the distal end of internal member 440 may be advantageously contacted by a fabric swab having a disinfectant applied thereto. As shown, the male connector 500 may be also present a substantially closed, distal end that may be swabbed with a disinfectant prior to interconnection with female connector 400.

Referring to FIG. 8, the internal member 440 may comprise a tubular shank member 442 fixedly interconnected to a tubular member 448 and a base member 444. For example, the shank member 442, base member 444 and tubular member 448 may be integrally formed. A fluid passageway extends from an opening 446 at a distal end of shank member 442 to a proximal end of the base member 444. As shown, base member 444 may be further provided with a proximal, tubular end portion having an internally threaded surface for selective interconnection with a compatible connector (e.g. a connector provided at an end of a tubing line that is interconnected or interconnectable with a medical liquid source). A resilient member 450 may be disposed about the distal end of shank member 442. Further, the resilient member 450 may extend along and between the tubular member 448 and shank member 442, wherein a proximal end of the resilient member 450 may be interconnected to the base member 444. In some arrangements, a distal end opening of tubular member 448 may be reduced so as to capture a distal end of resilient member 450 therewithin. The distal end of resilient member 450 may be slit (e.g. partially or fully pre-pierced) or piercable to allow the distal end of shank member 442 to forcibly penetrate therethrough when interconnected to female connector 500. The resilient member 450 may be provided with sidewall undulations 452 so as to facilitate depression of the resilient member 450 within tubular member 448 (e.g., in an accordion-like manner), and to otherwise bias the distal end of resilient member 450 to the position shown in FIG. 9A (i.e. substantially flush with or slightly projecting from a distal end opening of the tubular member 448) when not interconnected to male connector 500. As shown, the distal end of resilient member 450 substantially fills the distal opening of tubular member 448.

The outer collar 420 is provided with a first internal interconnection surface 426 for selective interconnection of the female connector 400 to male connector 500. More particularly, the internal interconnection surface 426 may comprise a threaded surface that is size/shaped for threadably engaging an interconnection surface 502 of male connector 500, e.g. a complimentary threaded surface 502 on the outside surface of male connector 500 as shown in FIG. 7.

Referring now to FIG. 9A, male connector 500 may comprise a tubular, outer member 520. A resilient member 510 may be provided at a reduced, distal end of the outer member 520. As illustrated, resilient member 510 may present a closed distal end on male connector 500. Resilient member 510 may be slit (e.g. prepierced) or piercable to allow the distal end of shank member 442 of female connector 400 to be forcibly penetrate therethrough when male connector 500 is interconnected to female connector 400. Male connector 500 further includes an tubular, internal member 530 secured within outer member 520. Internal member may be optionally sized to matingly receive a distal end of shank member 442 upon interconnection of female connector 400 to male connector 500.

FIGS. 9B-9D illustrate the progression of interconnection of female connector 400 and male connector 500. In FIG. 9B, outer collar 420 of female connector 400 has been rotatably advanced relative to internal member 440 and rotated into threadable engagement upon male connector 500. In the position shown in FIG. 9B, the distal end of internal member 440 has just contacted the distal end of resilient member 510. Of note, such interconnection may be achieved without the need to overcome any spring-loading force. Further, it may be noted that in the position shown in FIG. 9B, female connector 400 and male connector 500 may be advantageously mechanically interconnected without the establishment of a fluid interconnection therebetween.

In FIG. 9C outer collar 420 has been rotatably advanced further onto male connector 500 to an advanced interconnection position relative to that shown in FIG. 9B (e.g. by a user holding male connector 500 with one hand and rotatably advancing the outer collar 420 with another hand), thereby causing the distal end of resilient member 510 to depress resilient member 450 inwardly within tubular member 448 against the spring-loading force applied by resilient member 450. Further, the distal end of shank member 442 is shown forcibly-penetrated through the resilient member 450 and penetrating resilient member 510. Such forcible penetration is advantageously achieved in conjunction with the rotatable, threaded advancement of outer collar 420 of female connector 400 relative to male connector 500.

FIG. 9D Illustrates female connector 500 in a further interconnected position with male connector 400. That is, outer collar 420 has been rotatably advanced to a further advanced position relative to that shown in FIG. 9C, wherein a distal end of shank member 442 has sealably extended through resilient member 450 and resilient member 510 to a position within the distal end of internal member 530 of the male connector 500, thereby establishing a fluid interconnection between the female connector 400 and male connector 500. As shown, shank member 442 may be tapered and sized relative to the distal end of internal member 530 to facilitate the fluid interconnection therebetween.

As will be appreciated, in the position shown in FIG. 9D fluid transfer between the female connector 400 and male connector 500 may be carried out. For example, a liquid medication may be administered to a patient via the female connector 400, male connector 500 and an intravascular catheter interconnected thereto, followed by a saline flush solution administered therethrough. Thereafter, the female connector 400 and male connector 500 may be disconnected by rotation of outer collar 420 relative to the male connector 500. Upon doing so, the distal ends of resilient member 450 and resilient member 510 will each again be substantially closed due to their resilient nature. Subsequently, if/when a further administration of a medical liquid utilizing female connector 400 and/or male connector is desired, female connector 400 and/or male connector may be disinfected and reconnected as described in relation to FIG. 9A-9D.

FIGS. 10 and 11 illustrate another embodiment of a fluid connector comprising the present invention. In this embodiment, a male connector 600 is provided for selective interconnection and fluid transfer with a female connector 700, e.g., a female connector as described in U.S. Pat. No. 6,706, 022, hereby incorporated by reference in its entirety.

The male connector 600 includes an outer collar 620 that is supportably disposed about and interconnected with an internal member 640 for selective advancement and retraction relative thereto. For example, outer collar 620 may be slidably and rotatably disposed about internal member 640. In FIGS. 10 and 11 the outer collar 620 is shown in a retracted position so that a substantially closed, distal portion of the internal member 640 is exposed. In this position, the distal portion of internal member 640 may be readily contacted with a disinfectant. For example, a distal end and adjoining sidewall portion of the internal member 640 may be advantageously contacted by a fabric swab having a disinfectant applied thereto. As will be appreciated, the female connector 700 may present a substantially closed distal end that may also be readily swabbed with a disinfectant prior to interconnection with the male connector 600.

Referring to FIG. 11, internal member 640 may comprise a tubular main body 650 and a resilient, closed-end sheath 660 positioned about a distal portion 652 of the main body 650. The main body 650 may further include an enlarged proximal portion 654, wherein the proximal portion 654 extends through an opening 622 at a proximal end of the outer collar 620. The proximal portion 654 of main body 650 may be provided with an annular recess 656 that extends about and along the proximal portion 654 of the main body 650. The proximal portion 654, recess 656 and outer collar 620 may be sized so that a proximal end flange 624 of the outer collar 620 may travel along the recess 656 as outer collar 620 is advanced and retracted relative to internal member 640. As shown, the proximal end flange 624 may also serve to co-axially align the outer collar 620 and internal member 640, and to restrict the relative range of advancement/retraction to the length of the recess 656.

A proximal end of resilient sheath 660 is restrainably engaged within an annular groove 658 of the main body 650 (e.g. utilizing hoop strength at the proximal end of sheath 660 and/or by bonding and/or by capture between main body 650 and outer collar 620). A slit 662 may extend through the closed, distal end of the resilient sheath 660, wherein a distal end of the main body 650 may forcibly penetrate through the slit 662 at the distal end of the resilient sheath 660. As will be further described, upon advancement of the distal end of main body 650 through slit 662 a fluid passageway extending through main body 650 may be accessed for fluid transfer with the female connector 700 upon interconnection therewith. Upon retraction of the distal end of main body 650 through the slit 662 of resilient sheath 660, the distal end of flexible member 660 will automatically close at slit 662. In this regard, the resilient nature of resilient sheath 660 may provide the spring force for closure.

In medical applications, the proximal end 654 of main body 650 may be interconnected (e.g. bonded) to a tubing line that is fluidly interconnected or interconnectable with one or more sources medical liquid (e.g. liquid medication, saline solution, etc.) or with an intravascular catheter. In other arrangements, the proximal end 654 of main body 650 may be provided with a coupling member (e.g. a female luer connector) for selective interconnection with a compatible coupling member (e.g. a rotatable male luer) disposed at an end of a tubing line that is connected or connectable to one or more a medical liquids source(s) or to an intravascular catheter.

The outer collar 620 of male connector 600 includes a stepped-out portion at its distal end to matingly conform with the shape presented by a distal end of female connector 700. Further, the male connector 600 is provided with an interconnection surface 626 for selective interconnection of the male connector 600 with female connector 700. More particularly, and the interconnection surface 626 may be internally located proximal to said stepped-out portion and may comprise a threaded surface that is sized/shaped for threadably engaging a complimentary-threaded, external surface 702 on female connector 700 as shown in FIG. 10.

Referring now to FIGS. 12A-12D, the use and interconnection of male connector 600 to female connector 700 will be described in detail. Initially, and as shown in FIG. 12A, outer collar 620 may be located in a retracted position relative to internal member 640 (e.g. via a manual, one-hand operation by a user), thereby exposing a distal end portion of internal member 640 for application of a disinfectant thereto (e.g. via a manual, other-hand operation by the user). Similarly, disinfectant may be applied to a distal end of a resilient member 710 located within an opening at a distal end of a tubular member 720 comprising female connector 700 (e.g. via a manual, two-handed operation by the user).

As shown in FIG. 12A, tubular member 720 may comprise a proximal base portion 724 and distal end portion 728. The base portion 724 includes a proximal, tubular end that may be internally threaded for interconnection with a compatible coupler (e.g. for fluid interconnection to an intravascular catheter or medical liquid source(s)). The resilient member 710 of female connector 700 is of a tubular construction with a closed distal end, and may be interconnected at a proximal end to base portion 724 of the tubular member 720, wherein a fluid passageway extends from the proximal end of the base portion 724 through the resilient member 710 to a distal end thereof. As shown, an openable/closable slit 712 is provided through the distal end of resilient member 710. The resilient member 710 comprises sidewall undulations 714 and is otherwise sized relative to tubular member 720 so that the resilient sidewall member 710 may be slightly depressed within the tubular member 720 upon interconnection of the female connector 200 to male connector 600. The distal end portion 728 of tubular member 720 is shaped to interface with a distal end portion of the resilient member 710. In particular, the distal end portion 728 is stepped-in so as to restrain, or capture, the resilient member 710 within the tubular member 720. Of further note, the distal end portion 728 is shaped to allow the distal end of resilient member 710 to open and flex outward at slit 712 upon interconnection of the female connector 700 to the male connector 600. Due to the resilient nature of resilient member 710 the distal end thereof is maintained in the position shown in FIG. 12A when the female connector 700 is not interconnected to the male connector 600.

FIGS. 12B-12D illustrate the progression of interconnection of male connector 600 to female connector 700. In FIG. 12B, outer collar 620 has been axially advanced relative to internal member 640, (e.g. by a user holding female connector 700 with one hand and advancing the outer collar 620 with another hand), wherein the distal end of internal member 640 has just contacted the distal end of resilient member 710.

In FIG. 12C, outer collar 620 has been rotatably advanced onto female connector 700 (e.g. by a user holding female connector 700 with one hand and rotatably advancing the outer collar 620 with another hand), thereby causing the distal end of the main body 650 to forcibly-penetrate the resilient sheath 660 and depress resilient member 710 inwardly within female connector 700 against a spring-loading force applied by resilient member 710. Such action is advantageously achieved jointly with the rotatable, threaded advancement of outer collar 620 of male connector 600 relative to female connector 700.

FIG. 12D illustrates male connector 600 in a further interconnected position on female connector 700. That is, outer collar 620 has been rotatably advanced to a further advanced location relative to that shown in FIG. 12C, wherein the distal end of tubular member 720 has sealably engaged the spring-loaded, resilient sheath 660 of the internal member 640, and wherein the slit 712 of resilient member 710 has opened/flexed outward and the distal end of main body 650 has been forcibly penetrated through the slit 712 and is located within the tubular resilient member 710. As will be appreciated, in this position fluid transfer between male connector 600 and female connector 700 may be carried out.

For example, a liquid medication may be administered to a patient via the male connector 600, female connector 700 and an intravascular catheter interconnected thereto, followed by a saline flush solution administered therethrough. Thereafter, the male connector 600 and female connector 700 may be disconnected by rotation of the outer collar 620 relative to the female connector 700. Upon doing so, the distal ends of resilient sheath 660 and resilient member 710 will automatically close due to their resilient nature. Subsequently, if further administration of medical liquid is desired utilizing male connector 600 and/or female connector 700, the male connector 600 and/or female connector 700 may be disinfected and reconnected as described above in relation to FIGS. 12A-12D.

Figure 13:
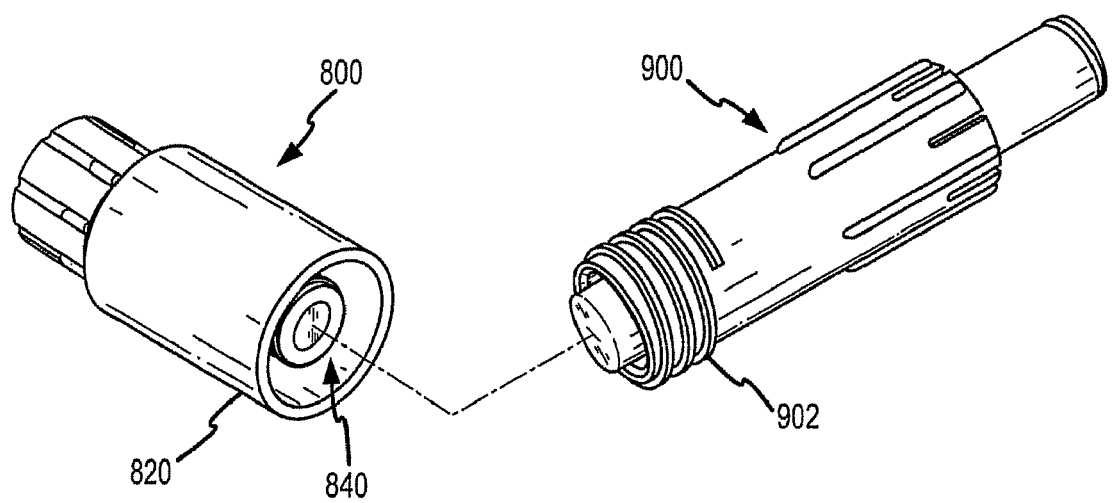
FIG. 13 illustrates opposing perspective views of another embodiment of an inventive female connector and a male connector interconnectable therewith.
Figure 14:
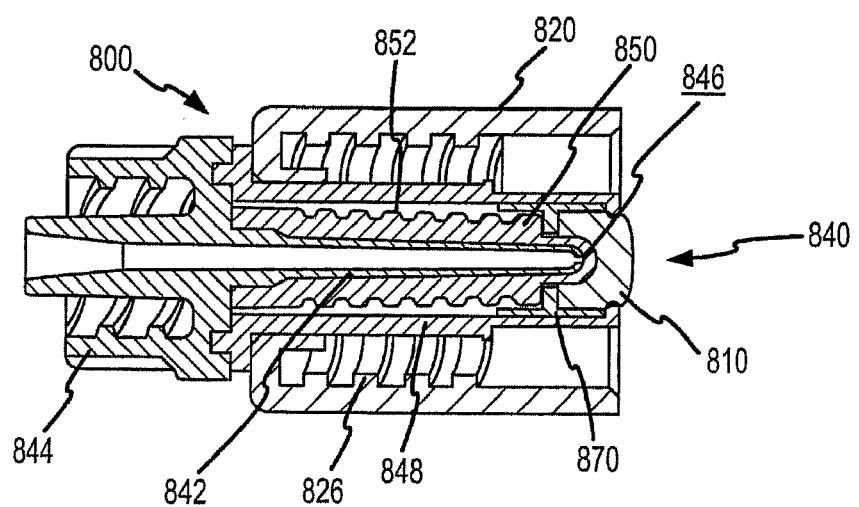
FIG. 14 is a cross sectional view of the female connector embodiment of FIG. 13.

FIGS. 13 and 14 illustrate another female connector 800 adapted for selective interconnection and fluid transfer with a male connector 900. As shown in FIG. 14, female connector 800 includes an outer collar 820 supportably disposed about and interconnected with an internal member 840 for selective advancement and retraction relative thereto. For example, outer collar 820 may be slidably and rotatably disposed about internal member 840. In FIGS. 13 and 14 the outer collar 820 is shown in a retracted position so that a substantially closed, distal end of the internal member 840 is exposed. In this position, the closed, distal end of internal member 840 may be disinfected or otherwise cleaned. For example, the distal end of internal member 840 may be advantageously contacted by a fabric swab having a disinfectant applied thereto. Similarly, disinfectant may be applied to a distal end of male connector 900.

Referring to FIG. 14, the internal member 840 may comprise a tubular shank member 842 fixedly interconnected to a tubular member 848 via a base member 844. For example, the shank member 842 and base member 844 may be integrally formed. A fluid passageway extends from an opening 846 at a distal end of shank member 842 to a proximal end of the base member 844. As shown, base member 844 may be further provided with a proximal tubular end portion having an internally threaded surface for selective interconnection with a compatible coupler (e.g. a coupler provided at an end of a tubing line that is interconnected or interconnectable with a medical liquid source or intravascular catheter). A resilient sheath 850 may be disposed about the shank member 842 and operatively interfaced with a resilient member 810 via an intermediate member 870. Resilient sheath 850 and resilient member 810 may be slit (e.g. pre-pierced) or pierceable to allow the distal end of shank member 842 to be forcibly advanced therethrough when interconnected to male connector 900. Resilient sheath 850 includes undulations 852 to apply a spring-loading force to resilient member 810 via intermediate member 870, wherein resilient member 810 is maintained in the position shown in FIG. 14 (i.e. within the distal end opening of female connector 800) when not interconnected to male connector 900.

The outer collar 820 is provided with a first internal interconnection surface 826 for selective interconnection of the female connector 800 to male connector 900. More particularly, and as shown in FIG. 14, the internal interconnection surface 826 may comprise a threaded surface that is sized/shaped for threadably engaging an interconnection surface 902 of male connector 900, e.g. a complimentary threaded surface 902 on the outside surface of male connector 900, as shown in FIG. 13.

Figure 15C:
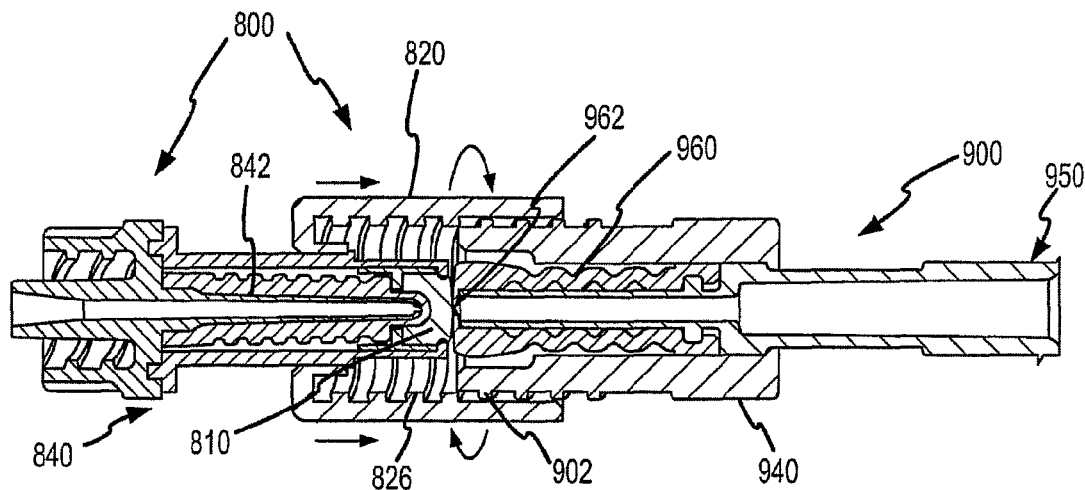

Referring now to FIGS. 15A-15E, the use and interconnection of female connector 800 to male connector 900 will be described in detail. Initially, and as shown in FIG. 15A, outer collar 820 may be located in the retracted position relative to internal member 840 (e.g. via a manual, one-hand operation by a user), thereby exposing a distal end of internal member 840 for application of a disinfectant thereto (e.g. via manual, other-hand operation by the user). Similarly, a disinfectant may be applied to a distal end of a resilient member 960 located within an opening at a distal end of a tubular member 940 comprising a female connector 900 (e.g. via a manual, two-handed operation by the user).

As shown in FIG. 15A, the male connector 900 may further comprise a tubular main body 950, wherein the resilient member 960 is positioned about a distal portion 952 of the main body 950. The main body 950 may further include an enlarged proximal portion 954, wherein the proximal portion 954 extends through an opening 942 at a proximal end of the tubular member 940. In the described embodiment, tubular member 940 is fixedly interconnected to the proximal portion 954 of the main body 950. However, it should be noted that in a modified arrangement, the main body 950 and tubular member 940 may be provided so that the tubular member 940 may be slidably and rotatably advanced and retracted relative to the main body 950. For example, the proximal portion 954 may be provided with an annular recess 956, wherein the proximal portion 954, recess 956 and tubular member 940 may be sized so that a proximal end flange 944 of the tubular member 940 may travel along the recess 956 as tubular member 940 is advanced and retracted relative to a main body 950.

Referring further to FIG. 15A, it can be seen that a proximal end of the resilient member 960 is restrainable engaged within an annular groove 958 of the main body 950 (e.g. utilizing hoop strength at the proximal end of resilient member 960 and/or bonding and/or by capture between main body 950 and tubular member 940). A slit 962 may extend through a closed, distal end of resilient member 960.

FIGS. 15B-15E illustrate the progression of interconnection of female connector 800 to male connector 900. In FIG. 15B, outer collar 820 of female connector 800 has been axially advanced relative to internal member 840, so that the distal end of internal member 840 has just contacted the distal end of resilient member 960 (e.g. by a user holding male connector 900 with one hand and advancing the outer collar 820 with another hand).

In FIG. 15C, outer collar 820 has been rotatably advanced further onto male connector 900 to an advanced interconnection position relative to FIG. 15B (e.g. by a user holding male connector 900 with one hand and rotatably advancing the outer collar 820 with another hand), thereby causing the distal end of resilient member 960 to begin to depress resilient member 810 inwardly within female connector 800 against the spring-loading force applied by resilient sheath 850 thereagainst. Further, the distal end of the main body 950 of the male connector 900 has begun to forcibly penetrate the slit 962 at the distal end of the resilient member 960.

Figure 15D:
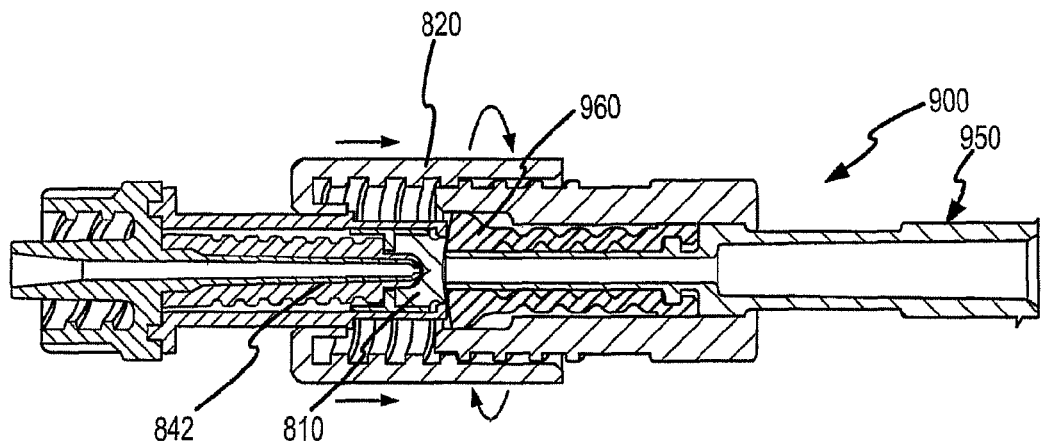

In FIG. 15D, outer collar 820 has been rotatably advanced to a further interconnected position on male connector 900. As illustrated, the distal end of main body 950 has now completely opened the slit 962 at the distal end of resilient member 960 and has further depressed the resilient member 810 within the female connector 800. In turn, the distal end of shank member 942 has begun to forcibly penetrate through the resilient sheath 850 and resilient member 810.

Figure 15E:
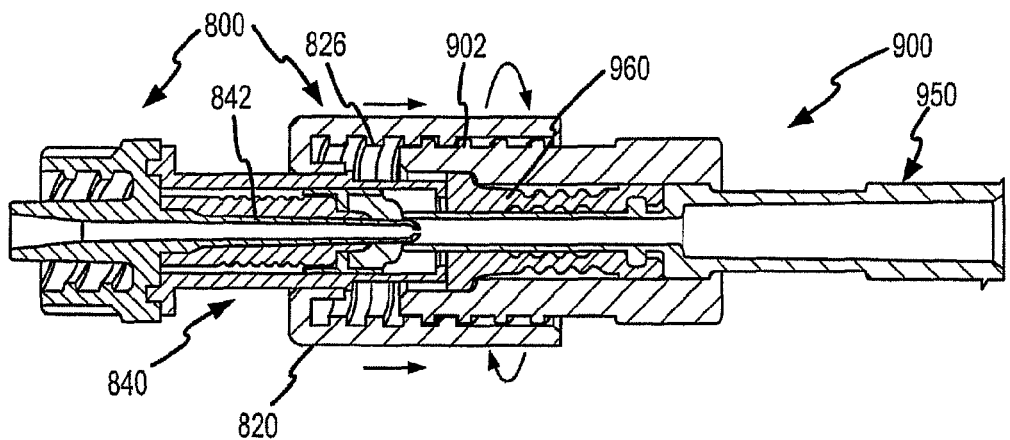

FIG. 15E Illustrates female connector 800 in a further interconnected position with male connector 900. That is, outer collar 820 has been rotatably advanced to a further advanced position relative to that shown in FIG. 15D, wherein a distal end of tubular main body 950 has sealably engaged the spring-loaded resilient member 810 and/or the distal end of tubular main body 848 has sealably engaged spring-loaded resilient member 960, and wherein a distal end of shank member 842 has forcibly penetrated through resilient sheath 850 and depressible member 810 to a position within the distal end of main body 950 of the male connector 900, thereby establishing a fluid interconnection between the female connector 800 and male connector 900. As shown, shank member 842 may be tapered and sized relative to distal end of main body 950 to facilitate the fluid interconnection therebetween. As will be appreciated, in this position fluid transfer between the female connector 800 and male connector 900 may be carried out.

For example, a liquid medication may be administered to a patient via the female connector 800, male connector 900 and an intravascular catheter interconnected thereto, followed by a saline flush solution administered therethrough. Thereafter, the female connector 800 and male connector 900 may be disconnected by rotation of outer collar 820 relative to the male connector 900. In so doing, the distal ends of depressible member 810 and resilient member 960 will substantially close due to their resilient nature. Subsequently, if/when further administration of a medical liquid is desired utilizing female connector 800 and/or male connector 900, the female connector 800 and/or male connector 900 may be disinfected and reconnected as described in relation to FIG. 15A-15D.

Figure 16:
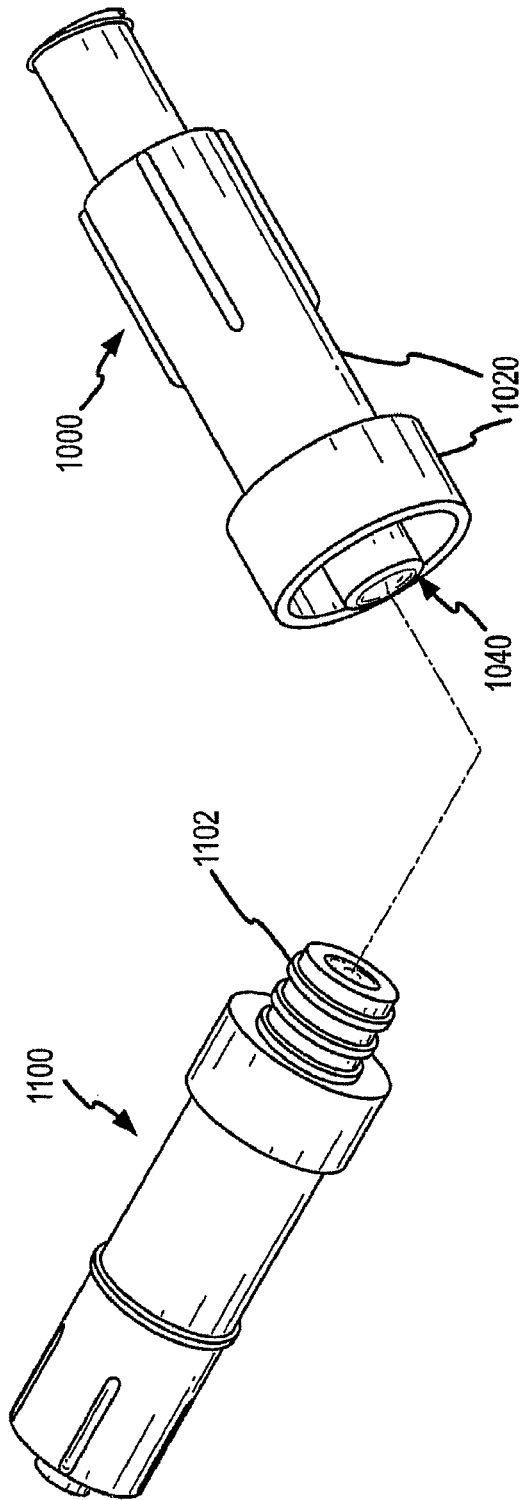
FIG. 16 illustrates opposing perspective views of another embodiment of an inventive male connector and a female connector interconnectable therewith.
Figure 17:
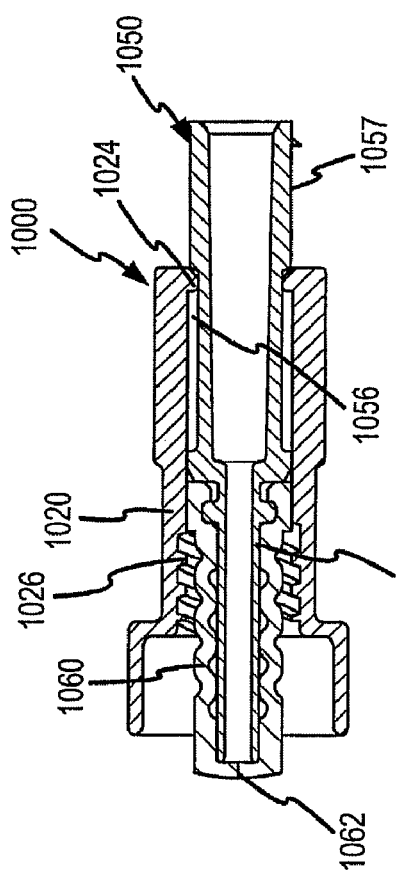
FIG. 17 is a cross sectional view of the male connector embodiment of FIG. 16.

FIGS. 16 and 17 illustrate another male connector embodiment. In this embodiment, male connector 1000 is provided for selective interconnection and fluid transfer with a female connector 1100. Male connector 1000 includes an outer collar 1020 that is supportably disposed about and interconnected with an internal member 1040 for selective advancement and retraction relative thereto. For example, outer collar 1020 may be slidably and rotatably disposed about internal member 1040. In FIGS. 16 and 17, the outer collar 1020 is shown in a retracted position so that a substantially closed, distal portion of the internal member 1040 is exposed. In this position, the distal portion of internal member 1040 may be readily contacted with a disinfectant. For example, a distal end and adjoining sidewall portion of the internal member 1040 may be advantageously contacted by a fabric swab having a disinfectant applied thereto. As will be appreciated, the female connector 1100 may also present a distal end that may also be readily swabbed with a disinfectant prior to interconnection with the male connector 1000.

Referring to FIG. 17, internal member 1040 may comprise a tubular main body 1050 and a resilient, closed-end sheath 1060 positioned about a distal portion 1052 of the main body 1050. The main body 1050 may further include an enlarged proximal portion 1054, wherein the proximal portion 1054 extends through an opening 1022 at a proximal end of the outer collar 1020. The proximal portion 1054 of main body 1050 may be provided with an annular recess 1056 that extends about and along the proximal portion 1054 of the main body 1050. The proximal portion 1054, recess 1056 and outer collar 1020 may be sized so that a proximal end flange 1024 of the outer collar 1020 may travel along the recess 1056 as outer collar 1020 is advanced and retracted relative to internal member 1040. As shown, the proximal end flange 1024 may also serve to co-axially align the outer collar 1020 and internal member 1040, and to restrict the relative range of advancement/retraction to the length of the recess 1056.

A proximal end of resilient sheath 1060 is restrainably engaged within an annular groove 1058 of the main body 1050 (e.g. utilizing hoop strength at the proximal end of sheath 1060 and/or by bonding and/or by capture between main body 1050 and outer collar 1020). A slit 1062 may extend through the closed, distal end of the resilient sheath 1060, wherein a distal end of the main body 1050 may forcibly penetrate therethrough. As will be further described, upon advancement of the distal end of main body 1050 through slit 1062 at the distal end of resilient sheath 1060, a fluid passageway extending through main body 1050 may be accessed for liquid transfer to/from the female connector 1100 upon interconnection therewith. Upon retraction of the distal end of main body 1050 through the slit 1062 of resilient sheath 1060, ring member 1070 may act to facilitate the closure of the distal end of resilient sheath 1060 at slit 1062. In this regard, the resilient nature of resilient sheath 1060 may provide the spring force for closure.

In medical applications, the proximal end 1054 of main body 1050 may be interconnected (e.g. bonded) to a tubing line that is fluidly interconnected or interconnectable with one or more sources medical liquid (e.g. liquid medication, saline solution, etc.) or with and intravascular catheter. In other arrangements, the proximal end 1054 of main body 1050 may be provided with a coupling member (e.g. a female luer connector) for selective interconnection with a compatible coupling member (e.g. a rotatable male luer) disposed at an end of a tubing line that is connected or connectable to one or more a medical liquids source(s) or to an intravascular catheter.

A distal portion of the outer collar 1020 of male connector 1000 is stepped-out to matingly conform with the shape presented by the distal end of female connector 1100. Further, the outer collar 1020 is provided with an interconnection surface 1026 for selective interconnection of the male connector 1010 with female connector 1100. More particularly, and as shown in FIG. 17, the interconnection surface 1026 may be internally located proximal to the stepped-out portion, and may comprise a threaded surface 1026 that is sized/shaped for threadably engaging a complimentary-threaded, external surface 1102 on female connector 1100, as shown in FIG. 16.

In this regard, and referring now to FIGS. 18A-18D, the use and interconnection of male connector 1000 to female connector 1100 will be described in detail. Initially, and as shown in FIG. 18A, outer collar 1020 may be located in a retracted position relative to internal member 1040 (e.g. via a manual, one-hand operation by a user), thereby exposing a distal end portion of internal member 1040 for application of a disinfectant thereto (e.g. via a manual, other-hand operation by the user). Similarly, disinfectant may be applied to a distal end of a resilient member 1110 located within an opening at a distal end of a tubular member 1120 comprising female connector 1100 (e.g. via a manual, two-handed operation by the user).

As shown in FIG. 18A, the resilient member 1110 of the female connector 1100 may be interconnected at a proximal end to the tubular member 1120. For example, the resilient member 1110 may be interconnected at a proximal end to a base portion 1124 of tubular member 1120. The base portion includes a proximal, tubular end that may be internally threaded for interconnection to a compatible coupler of a tubing line (e.g., interconnected or interconnectable to an intravascular catheter or medical liquid source(s)). As illustrated, a fluid passageway extends from the proximal end of base member 1124 to the distal end of into the tubular member 1120. Of note, the resilient member 1110 may be sized relative to the tubular member 1120 so that the resilient member 1110 is captured therein and so that a portion of the resilient member 1120 may be deflected within the tubular member 1120 in response to being depressed at a distal end thereof. In other embodiments, the resilient member 1110 may comprise a compressible material that compresses upon the application of a force applied to a distal end thereof. In any case, due to the resilient nature of resilient member 1110 the distal end thereof is maintained in the position shown in FIG. 18A when the female member 1100 is not interconnected to male connector 1000.

FIGS. 18B-18D illustrate the progression of interconnection of male connector 1000 to female connector 1100. In FIG. 18B, outer collar 1000 has been axially advanced relative to internal member 1040 (e.g. by a user holding female connector 1020 with one hand and advancing the outer collar 1020 with another hand). In the position shown in FIG. 18B, the distal end of internal member 1040 has just contacted the distal end of resilient member 1110.

In FIG. 18C, outer collar 1020 has been rotatably advanced onto female connector 1100 (e.g. by a user holding female connector 1020 with one hand and rotatably advancing the outer collar 1020 with another hand), thereby causing the distal end of main body 1050 to forcibly penetrate through slit 1062 of resilient sheath 1060. Such forcible penetration is advantageously achieved jointly with the rotatable, threaded advancement of outer collar 1020 of male connector 1000 relative to female connector 1100.

FIG. 18D illustrates male connector 1000 in a further interconnected position on female connector 1100. That is, outer collar 1020 has been rotatably advanced to a further advanced location relative to that shown in FIG. 18C, wherein a distal end of tubular member 1120 has sealably engaged spring-loaded, resilient sheath 1060, and wherein the distal end of main body 1050 has depressed and caused resilient member 1110 to deflect within the tubular member 1120. As will be appreciated, in this position fluid transfer between male connector 1000 and female connector 1100 may be carried out.

For example, in medical applications a liquid medication may be administered to a patient via the male connector 1000, female connector 1100 and an intravascular catheter interconnected thereto, followed by a saline flush solution administered therethrough. Thereafter, the male connector 1000 and female connector 1100 may be disconnected by rotation of the outer collar 1020 relative to the female connector 1100. In so doing, the distal ends of resilient sheath 1060 and female connector 1100 will automatically close. Subsequently, if further administration of medical liquid is desired utilizing male connector 1000 and/or female connector 1100, the male connector 1000 and/or female connector 1100 may be disinfected and reconnected as described above in relation to FIGS. 18A-18D.

FIGS. 19 and 20 illustrate another embodiment of an inventive female connector 1200 adapted for selective interconnection and fluid transfer with a male connector 1300. In this regard, male connector 1200 is similar to the female connector described in U.S. Pat. No. 5,782,816, modified to include an advanceable/retractable outer collar.

That is, male connector 1200 includes an outer collar 1220 supportably disposed about and interconnected with an internal member 1240 for selective advancement and retraction relative thereto. In FIGS. 19 and 20, the outer collar 1220 is shown in a retracted position so that a substantially closed, distal end of the internal member 1240 is exposed. In this position, the closed, distal end of internal member 1240 may be disinfected or otherwise cleaned. For example, the distal end of internal member 1240 may be advantageously contacted by fabric swab having a disinfectant applied thereto. As shown, male connector 1300 may also present a substantially closed, distal end that may be swabbed with a disinfectant prior to interconnection with female connector 1200.

Referring to FIG. 20, the internal member 1240 may include a resilient member 1210 captured within a tubular member 1240. In the later regard, tubular member 1240 may include a proximal base portion 1244 and distal end portion 1248, wherein a fluid passageway extends from the distal end to the proximal end of the tubular member 1240. As shown, the proximal end of base portion 1224 may be provided with internal threading for selective interconnection to a compatible coupler.

Figure 21C:
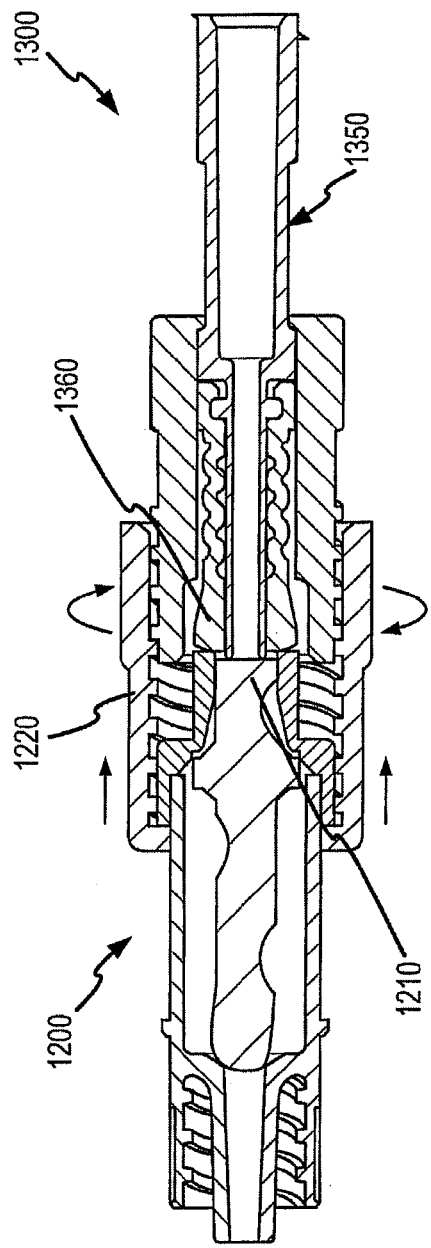

Referring now to FIGS. 21A-21D, the use and interconnection of female connector 1200 to male connector 1300 will be described in detail. Initially, and as shown in FIG. 21A, outer collar 1220 may be located in the retracted position relative to internal member 1240 (e.g. via a manual, one-hand operation by a user), thereby exposing a distal end of internal member 1240 for application of a disinfectant thereto (e.g. via manual, other-hand operation by the user). Similarly, a disinfectant may be applied to a distal end of a resilient member 1360 located within an opening at a distal end of a tubular member 1320 comprising the male connector 1300 (e.g. via a manual, two-handed operation by the user).

As shown in FIG. 21A, the male connector 1300 may further comprise a tubular main body 1350, wherein the resilient member 1360 is positioned about a distal portion 1352 of the main body 1350. The main body 1350 may further include an enlarged proximal portion 1354, wherein the proximal portion 1354 extends through an opening 1322 at a proximal end of the tubular member 1320. In the described embodiment, tubular member 1320 is fixedly interconnected to the proximal portion 1354 of the main body 1350. However, it should be noted that in a modified arrangement, the main body 1350 and tubular member 1320 may be provided so that the tubular member 1320 may be advanced and retracted relative to the main body 1350. For example, the proximal portion 1354 may be provided with an annular recess 1356, wherein the proximal portion 1354, recess 1356 and tubular member 1320 may be sized so that a proximal end flange 1324 of the tubular member 1340 may travel along the recess 1356 as tubular member 1340 is advanced and retracted relative to a main body 1350.

Referring further to FIG. 15A, it can be seen that a proximal end of the resilient member 1360 is restrainably engaged within a annular groove 1358 of the main body 1350 (e.g. utilizing hoop strength at the proximal end of resilient member 1360 and/or bonding and/or by capture between main body 1350 and tubular member 1320). A slit 1362 may extend through the closed, distal end of resilient member 1360.

Figure 21D:
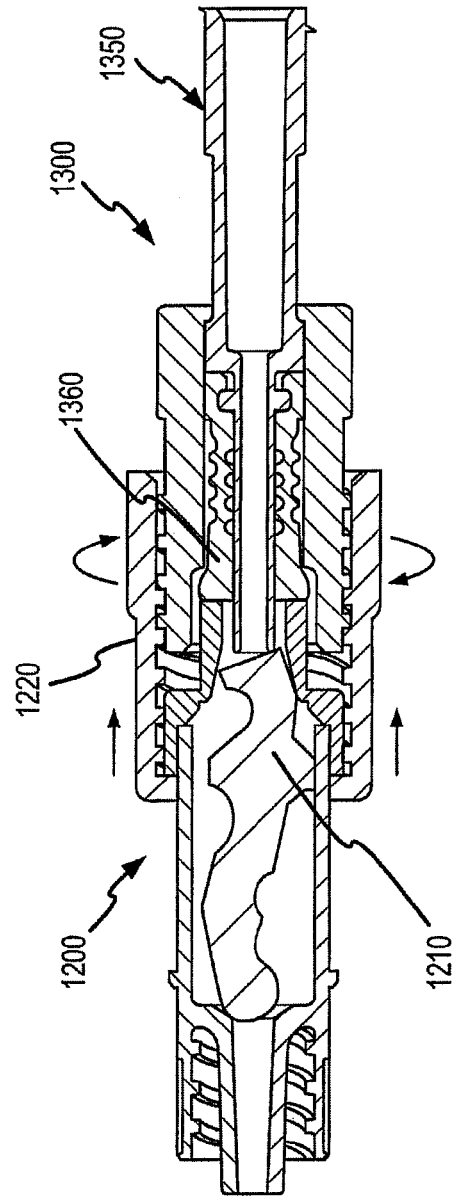

FIGS. 21B-21D illustrate the progression of interconnection of female connector 1200 to male connector 1300. In FIG. 21B, outer collar 1220 of female connector 1200 has been advanced relative to internal member 1240 distal end of internal member 1240 has just contacted the distal end of resilient member 1360.

In FIG. 21C, outer collar 1220 has been rotatably advanced further onto male connector 1300 (e.g. by a user holding male connector 1300 with one hand and rotatably advancing the outer collar 1220 with another hand), thereby causing the distal end of main body 1350 to forcibly-penetrate through the slit 1362 of resilient member 1360. Such forcible penetration is advantageously achieved in conjunction with the rotatable, threaded advancement of outer collar 1220 of female connector 1200 relative to male connector 1300.

FIG. 21D Illustrates female connector 1200 in a further interconnected position with male connector 1300. That is, outer collar 1220 has been rotatably advanced to a further advanced position relative to that shown in FIG. 21C, wherein a distal end of tubular member 1240 has sealably engaged spring-loaded, resilient member 1360, and wherein a distal end of main body 1350 has projected through resilient member 1360 to depress and deflect depressible member 1210 within the female connector 1200. As will be appreciated, in this position fluid transfer between the female connector 1200 and male connector 1300 may be carried out.

For example, in medical applications a liquid medication may be administered to a patient via the female connector 1200, male connector 1300 and an intravascular catheter interconnected thereto, followed by a saline flush solution administered therethrough. Thereafter, the female connector 1200 and male connector 1200 may be disconnected by rotation of outer collar 1220 relative to the male connector 1300. In so doing, the distal ends of female connector 1200 and resilient member 1360 will automatically close. Subsequently if a further administration of medical liquid is desired utilizing female connector 1200 and/or male connector 1300, the female connector 1200 and/or male connector 1300 may be disinfected and reconnected as described in relation to FIG. 21A-21D.

Figure 22:
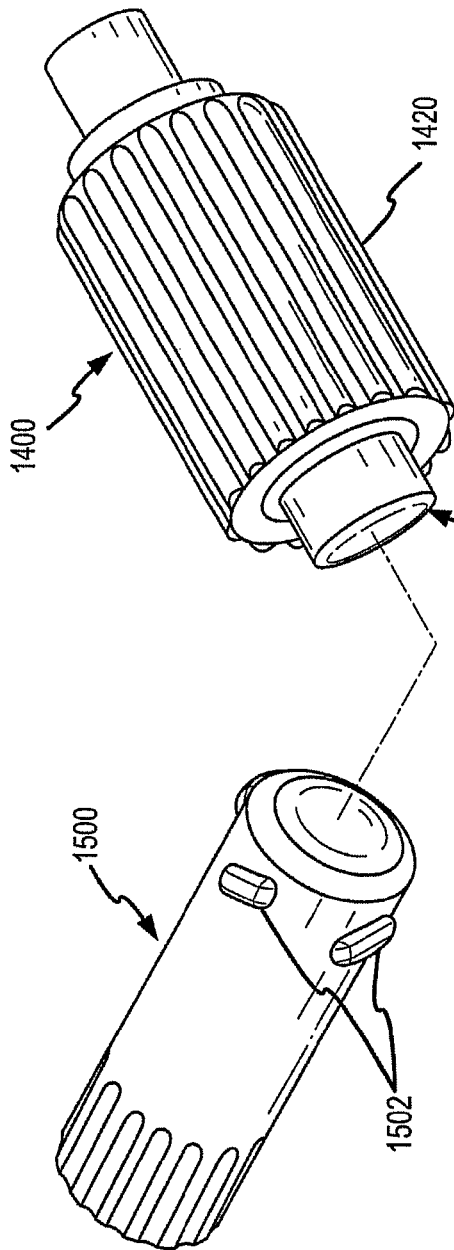
FIG. 22 illustrates opposing perspective views of another embodiment of an inventive female connector and a male connector interconnectable therewith.
Figure 23:
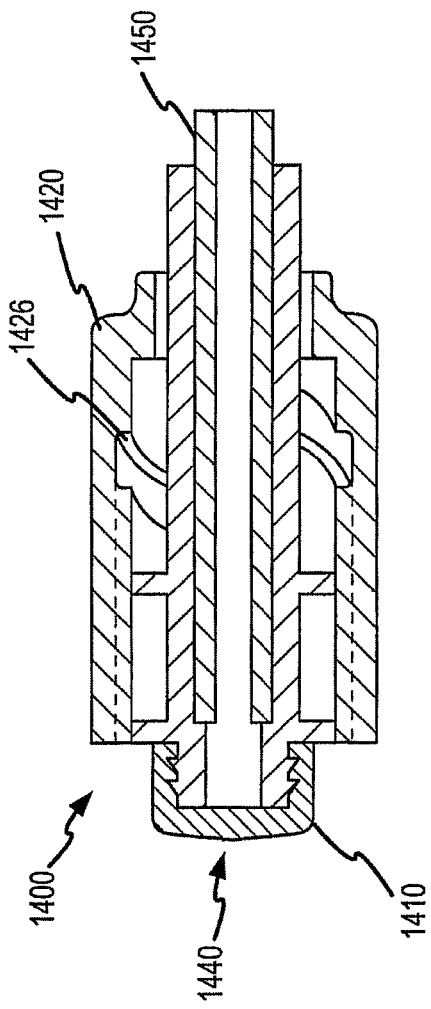
FIG. 23 is a cross sectional view of the female connector embodiment of FIG. 22.

FIGS. 22 and 23 illustrate another embodiment of a female connector 1400 adapted for selective interconnection and fluid transfer with a male connector 1500. As shown in FIG. 23, female connector 1400 includes an outer collar 1420 that is supportably disposed about and interconnected with an internal member 1440 for selective advancement and retraction relative thereto. For example, outer collar 1420 may be slidably and rotatably disposed about internal member 1440. In FIGS. 22 and 23 the outer collar 1420 is shown in a retracted position so that a substantially closed, distal end of the internal member 1440 is readily accessible. In this position, the closed, distal end of internal member 1440 may be disinfected or otherwise cleaned. For example, the distal end of internal member 1440 may be advantageously contacted by a fabric swab having a disinfectant applied thereto. As shown, the male connector 1500 may be also present a closed, distal end that may be swabbed with a disinfectant prior to interconnection with female connector 1400.

Referring to FIG. 23, the internal member 1440 of female connector 1400 may comprise a tubular main body 1450 that defines a fluid passageway. Further, a resilient member 1410 may be disposed about a distal end of the main body 1450, wherein a closed, distal end may be presented for swabbing operations. One or a series of outward projections 1452 may be provided on the main body 1450 so as to maintain the main body 1450 in an axially centered position relative to outer collar 1420, and so as to limit the travel of outer collar 1420 relative to main body 1450.

The outer collar 1420 is provided with an internal interconnection surface 1426 for selective interconnection of the female connector 1400 to male connector 1500. More particularly, the internal interconnection surface 1426 may comprise a threaded surface that is size/shaped for threadably engaging an interconnection surface 1502 of male connector 1500 as shown in FIG. 22. In the latter regard, interconnection surface 1502 of male connector 1500 may be defined by a plurality of projections that are spaced around the periphery of the male connector 1500. Such projections 1502 are disposed at an angle to correspond with the threading angle presented by internal interconnection surface 1426 of the female connector 1400. Of further note, female connector 1400 includes a plurality of channels (shown by phantom lines) for slidably receiving the projections 1502 on male connector 1500.

Referring now to FIG. 24A, the male connector 1500 may comprise a tubular shank member 1542 fixedly interconnected to a tubular member 1548 and a base member 1544. For example, the shank member 1542, base member 1544 and outer member 1548 may be integrally formed. A fluid passageway extends from an opening 1546 at a distal end of shank member 1542 to a proximal end of the base member 1544. As shown, base member 1544 may be provided with a proximal, tubular end portion having an internally threaded surface for selective interconnection with a compatible coupler (e.g. a coupler provided at an end of a tubing line that is interconnectable with a patient IV catheter). A resilient member 1550 may be disposed about the distal end of shank member 1542. Further, the resilient member 1550 may extend along and between the tubular member 1548 and shank member 1542, wherein a proximal end of the resilient member 1550 may be interconnected to the base member 1544. A distal end of resilient member 1550 may be slit (e.g. partially or fully pre-pierced) or piercable to allow the distal end of shank member 1542 to forcibly penetrate therethrough when interconnected to female connector 1400. The resilient member 1550 may be further provided with undulations 1552 so as to facilitate depression of the resilient member 1550 within tubular member 1548 (e.g., in an accordion like manner), yet bias the distal end of resilient member 1550 to the position shown in FIG. 24A (i.e. substantially flush with and filling the opening at the distal end of the tubular member 1548) when not interconnected to female connector 1400.

Figure 24C:
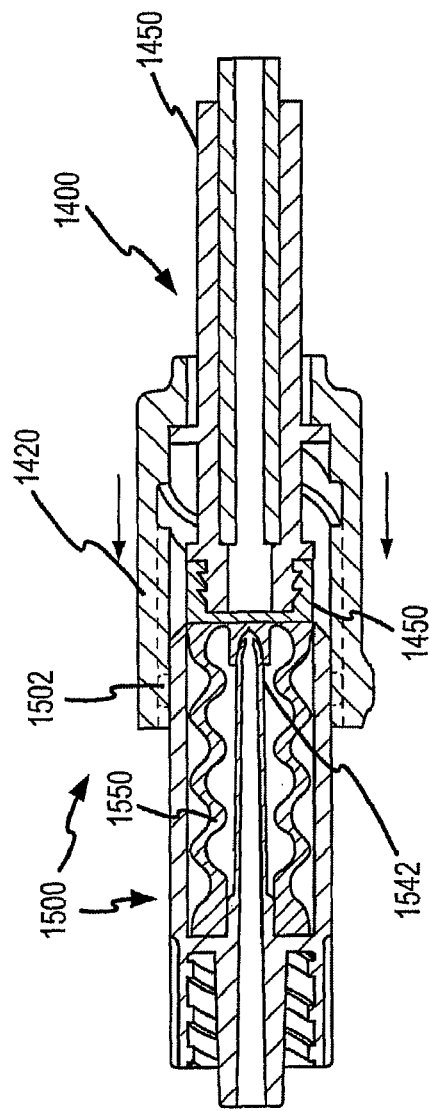
Figure 24D:
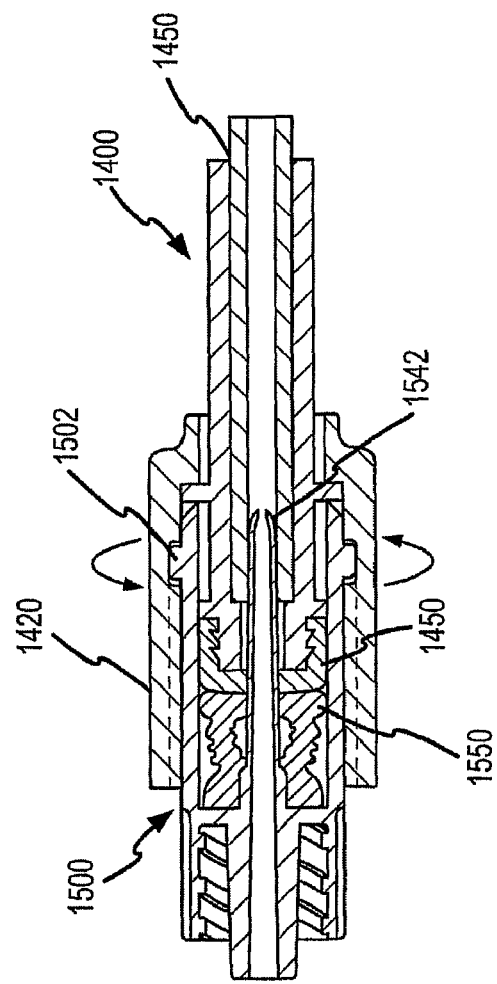

FIGS. 24B-24D illustrate the progression of interconnection of female connector 1400 and male connector 1500. In FIG. 24B, outer collar 1420 of female connector 1400 has been axially advanced relative to internal member 1440. In the position shown in FIG. 24B, the substantially closed, distal end of internal member 1440 has just contacted the distal end of resilient member 1550.

In FIG. 24C, outer collar 1420 has been axially advanced on to male connector 1500 (e.g. by a user holding male connector 1500 with one hand and advancing the outer collar 1420 with another hand). In so doing, the projections 1502 of the male connector 1500 have been aligned with advanced through the channels of collar 1420, as shown with phantom lines in FIG. 24C.

FIG. 24D Illustrates female connector 1400 in an interconnected position with male connector 1500. That is, outer collar 1420 has been rotatably advanced so that the threaded surface 1426 has threadably engaged the angled projections 1502. In conjunction with such action, a distal end of shank member 1542 has forcibly penetrated through resilient member 1550 and sealably penetrated through resilient member 1410 to a location within the distal end of main body 1450 of the female connector 1400, thereby establishing a fluid interconnection. As shown, shank member 1442 may be tapered and sized relative to the distal end of main body 1450 to facilitate the fluid interconnection therebetween.

As will be appreciated, in the position shown in FIG. 24D fluid transfer between the female connector 1400 and male connector 1500 may be carried out. For example, in medical applications, a liquid medication may be administered to a patient via the female connector 1400, male connector 1500 and an intravascular catheter interconnected thereto, followed by a saline flush solution administered therethrough. Thereafter, the female connector 1400 and male connector 1500 may be disconnected by rotation of outer collar 1420 relative to the male connector 1500. In so doing, the distal ends of resilient member 1410 and resilient member 1550 automatically close due to their resilient nature. Subsequently, if/when a further administration of a medical liquid is desired using female connector 1400 and/or male connector 1500, female connector 1400 and/or male connector 1500 may be disinfected and reconnected as described in relation to FIG. 24A-24D.

Figure 25:
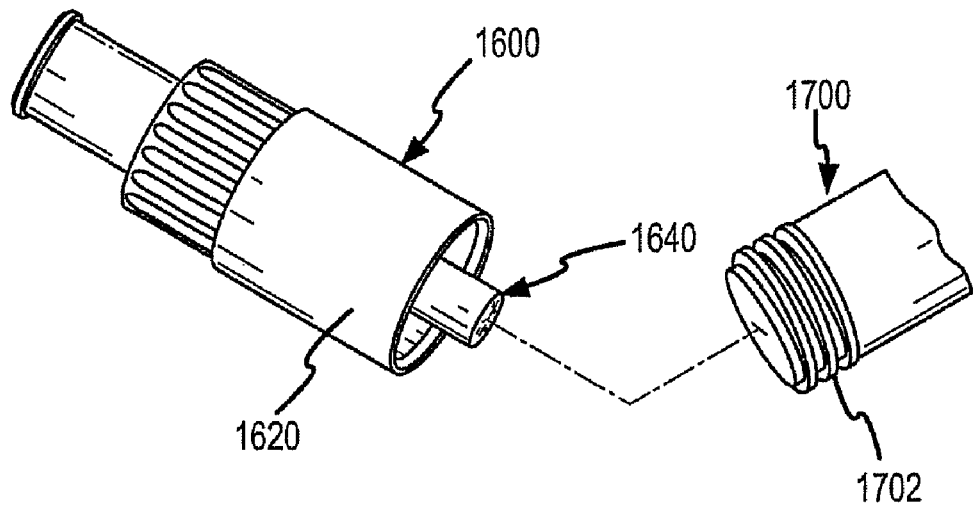
FIG. 25 illustrates opposing perspective views of another embodiment of an inventive male connector and a female connector interconnectable therewith.
Figure 26:
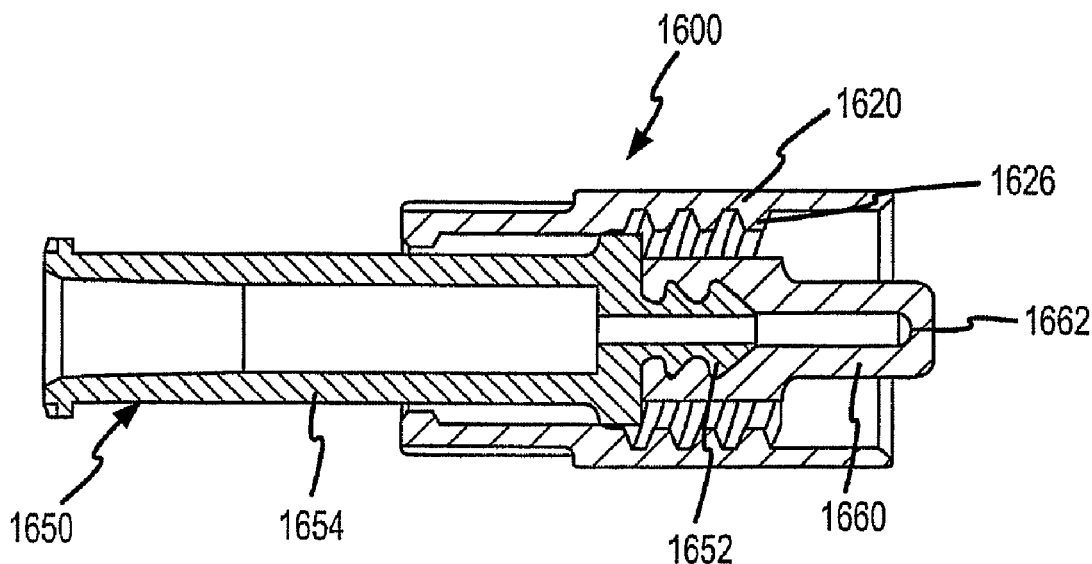
FIG. 26 is a cross sectional view of the male connector embodiment of FIG. 25.

FIGS. 25 and 26 illustrate another embodiment of a male connector 1600 adapted for fluid connection with a female connector 1700. The male connector 1600 includes an outer collar 1620 that is supportably disposed about and interconnected with an internal member 1640 for selective advancement and retraction relative thereto. For example, collar 1620 may be rotatably and slidably advanced and retracted relative to internal member 1640. In FIGS. 25 and 26, the outer collar 1620 is shown in a retracted position so that a substantially closed, distal portion of the internal member 1640 is exposed. In this position, the distal portion of internal member 1640 may be readily contacted with a disinfectant. For example, a distal end and adjoining sidewall portion of the internal member 1640 may be advantageously contacted by a fabric swab having a disinfectant applied thereto. As will be appreciated, the exemplary female connector 1700 may present a substantially closed, distal end that may also be readily swabbed with a disinfectant prior to interconnection with the male connector 1600.

Referring to FIG. 26, internal member 1640 may comprise a tubular main body 1650 and closed end, resilient member 1660 interconnected to a distal portion 1652 of the main body

1650, wherein a fluid passageway is defined through the main body 1650 and resilient member 1660. An openable/closeable slit 1662 may be provided at a distal end of resilient member 1660. The main body 1650 may further include an enlarged proximal portion 1654, wherein the proximal portion 1654 extends through an opening 1622 at a proximal end of the outer collar 1620. The proximal portion 1654 of main body 1650 may be provided with an annular recess 1656 that extends about and along the proximal portion 1654 of the main body 1650. The proximal portion 1654, recess 1656 and outer collar 1620 may be sized so that a proximal end flange 1624 of the outer collar 1620 may travel along the recess 1656 as outer collar 1620 is advanced and retracted relative to internal member 1640. As shown, the proximal end flange 1624 may also serve to co-axially align the outer collar 1620 and internal member 1640, and to restrict the relative range of advancement/retraction to the length of the recess 1656.

A proximal end of resilient member 1660 is restrainably engaged within annular grooves 1658 of the main body 1650 (e.g. utilizing hoop strength at the proximal end of resilient member 1660 and/or by bonding). A slit 1662 may extend through the closed, distal end of the resilient member 1660.

In medical applications, the proximal end 1654 of main body 1650 may be interconnected (e.g. bonded) to a tubing line that is fluidly interconnected or interconnectable with one or more sources medical liquid (e.g. liquid medication, saline solution, etc.) or with an intravascular catheter. In other arrangements, the proximal end 1654 of main body 1650 may be provided with a coupling member (e.g. a female luer connector) for selective interconnection with a compatible coupling member (e.g. a rotatable male luer) disposed at an end of a tubing line that is connected or connectable to one or more a medical liquids source(s) or to an intravascular catheter.

The outer collar 1620 of male connector 1600 is provided with an interconnection surface 1626 for selective interconnection of the male connector 1600 with female connector 200. More particularly, the interconnection surface 1626 may be internally located and may comprise a threaded surface that is sized/shaped for threadably engaging a complimentary-threaded, external surface 1702 on female connector 1700 as shown in FIG. 25.

Figure 27A:
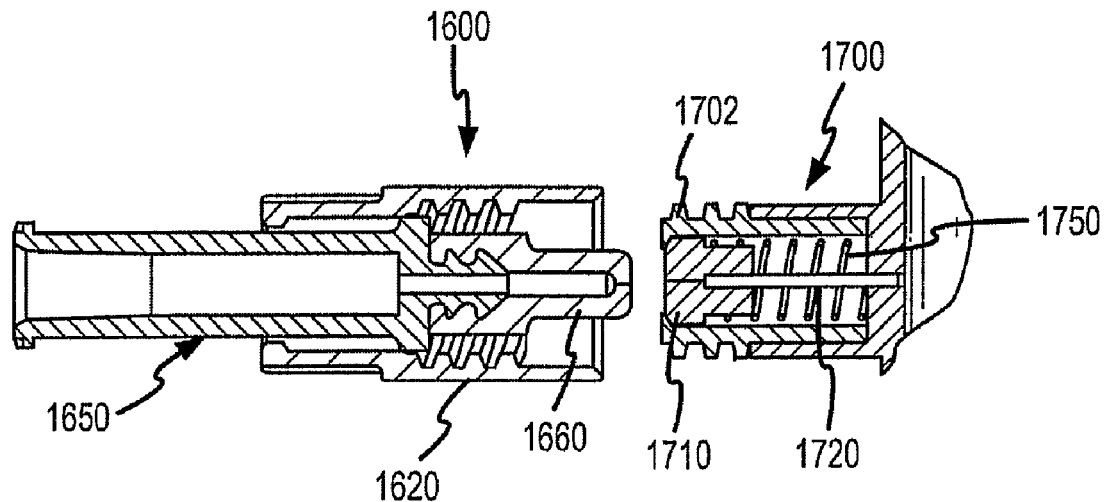
FIGS. 27A-27D are cross sectional views of the male connector embodiment and female connector of FIG. 25, shown in progressive stages of interconnection.

In this regard, and referring now to FIGS. 27A-27D, the use and interconnection of male connector 1600 to female connector 1700 will be described in detail. Initially, and as shown in FIG. 27A, outer collar 1620 may be located in a retracted position relative to internal member 1640 (e.g. via a manual, one-hand operation by a user), thereby exposing a distal end portion of internal member 1640 for application of a disinfectant thereto (e.g. via a manual, other-hand operation by the user). Similarly, disinfectant may be applied to a distal end of a resilient member 1710 located within an opening at a distal end of a tubular member 1720 comprising female connector 1700 (e.g. via a similar manual, two-handed operation by the user).

As shown in FIG. 27A, female connector 1700 may include a tubular member 1720 that is fixedly interconnected to and extends through a sidewall of a fluid channel 1780. A distal end of tubular member 1720 extends into the resilient member 1710. Further, the resilient member 1710 may be slit (e.g. pre-pierced) or pierceable through its distal end to allow the distal end of tubular member 1720 to be forcibly advanced therethrough when interconnected to male connector 1600. A spring member 1750 (e.g. a helical spring) is provided to apply a spring-loading force to resilient member 1710, wherein resilient member 1710 is maintained in the position shown in FIG. 27A (i.e. within the distal end opening of female connector 1700) when not interconnected to male connector 1600.

Figure 27B:
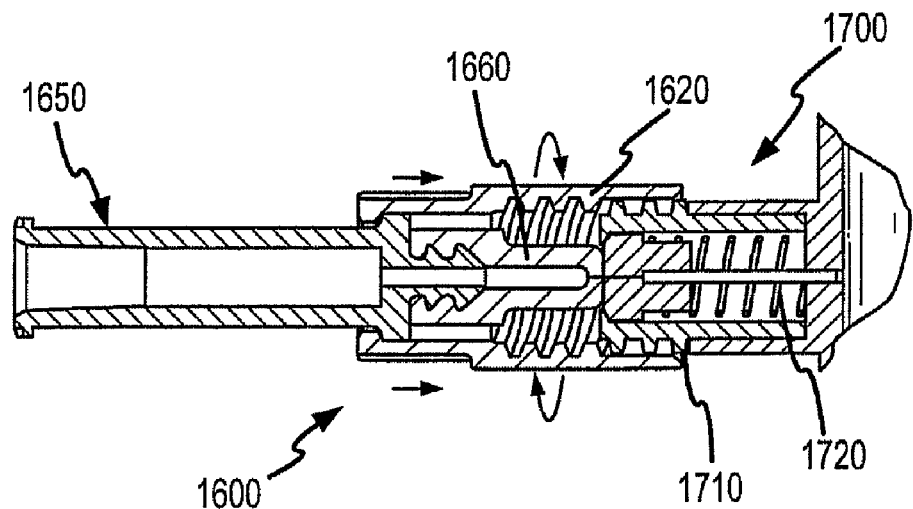
Figure 27C:
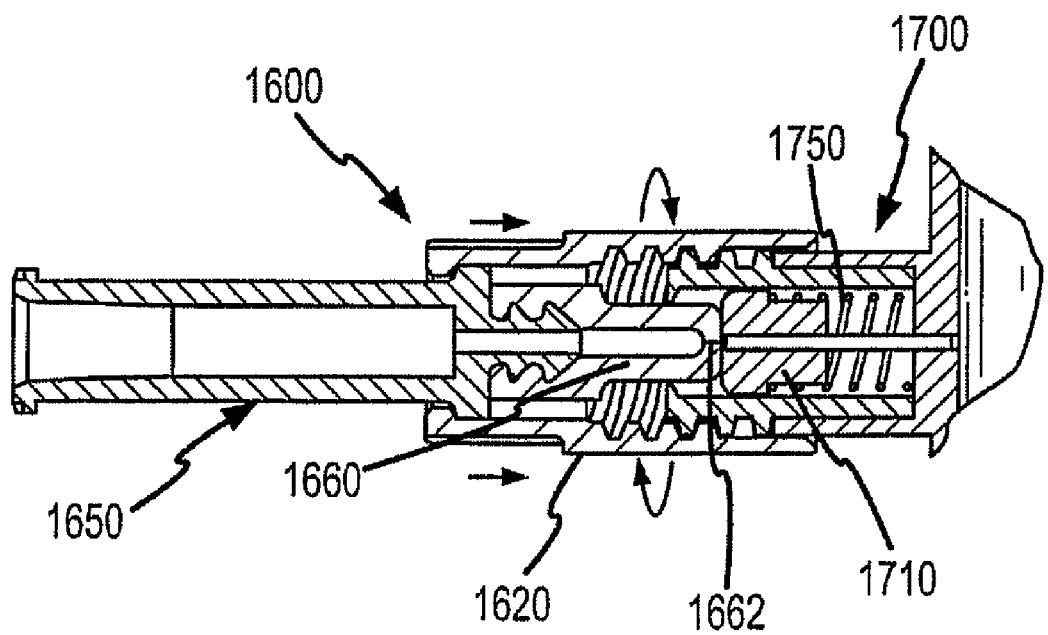
Figure 27D:
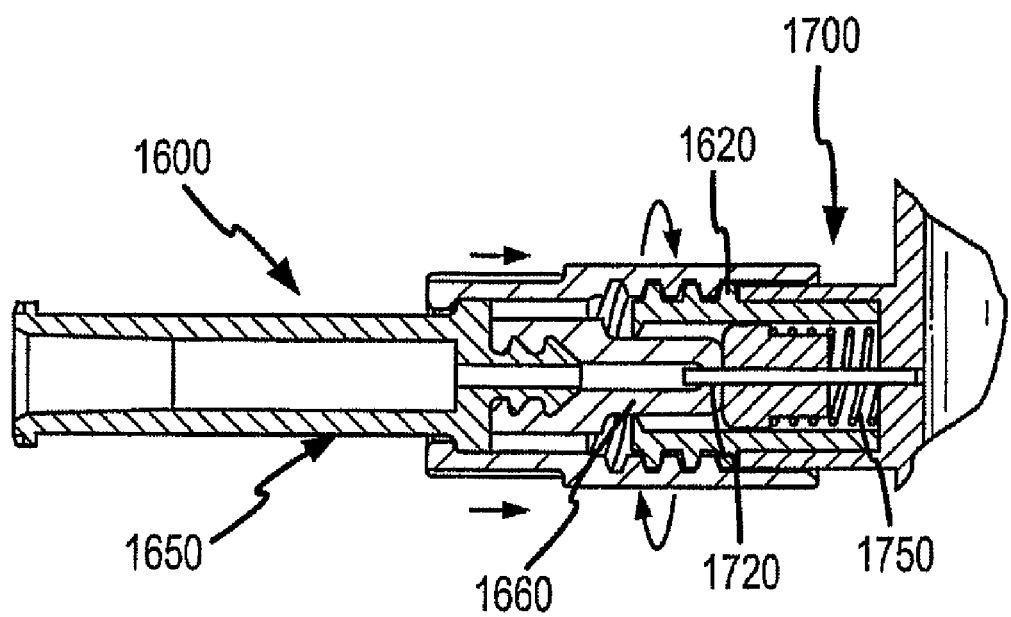

FIGS. 27B-27D illustrate the progression of interconnection of male connector 1600 to female connector 1700. In FIG. 27B, outer collar 1600 has been advanced relative to internal member 1640 and threadably rotated to an initial interconnection position relative to female connector 1700. In the position shown in FIG. 27B, the distal end of internal member 1640 has just contacted the distal end of depressible member 1710. Of note, such an initial interconnection position may be achieved without the need to overcome any spring-loading force. Further, it may be noted that in the position shown in FIG. 24B, the male connector 1600 and female connector 1700 may be advantageously mechanically interconnected without the establishment of a fluid interconnection therebetween. Such advantages may be realized in the illustrated arrangement due to the distally offset location of the distal end of the interconnection surface 1626 relative to the distal end of the internal member 1640 when outer collar 1620 is in an advanced position. In other modified arrangements the distal end of interconnection surface 1626 may be located so as to be aligned or proximally offset relative to the distal end of internal member 1640 when the outer collar 1620 is in an advanced position. As will be appreciated, such modified arrangements may provide for the contemporaneous establishment of mechanical and fluid interconnections between the modified male connector and a female connector.

In FIG. 27C, outer collar 1620 has been rotatably onto female connector 1700 to an advanced interconnection position relative to FIG. 24B (e.g. by a user holding female connector 1620 with one hand and rotatably advancing the outer collar 1620 with another hand), thereby causing the distal end of internal member 1640 to depress the resilient member 1710 so that the distal end of tubular member 1720 penetrates through of the resilient member 1710. Such penetration is advantageously achieved jointly with the rotatable, threaded advancement of outer collar 1620 of male connector 1600 relative to female connector 1700.

FIG. 27D illustrates male connector 1600 in a further interconnected position on female connector 1700. That is, outer collar 1620 has been rotatably advanced to a further advanced location relative to that shown in FIG. 27C, wherein the distal ends of resilient members 1660 and 1710 have sealably engaged, and wherein the distal end of tubular member 1720 has penetrated entirely through resilient member 1710 and through slit 1662 of resilient member 1660 to access the passageway therewithin. As will be appreciated, in this position fluid transfer between male connector 1600 and female connector 1700 may be carried out.

For example, a liquid medication may be administered to a patient via the male connector 1600, female connector 1700 and an intravascular catheter interconnected thereto, followed by a saline flush solution administered therethrough. Thereafter, the male connector 1600 and female connector 1700 may be disconnected by rotation of the outer collar 1620 relative to the female connector 1700. In so doing, the distal ends of resilient member 1660 and resilient member 1710 will automatically close due to their resilient nature. Subsequently, if further administration of medical liquid is desired utilizing male connector 1600 and/or female connector 1700, the male connector 1600 and/or female connector 1700 may be disinfected and reconnected as described above in relation to FIGS. 27A-27D.

The above-described embodiments and usages thereof are for exemplary purposes only. Various modifications, extensions and adaptations of the present invention will be appar-

What is claimed is:

1. A method for handling a first fluid connector, comprising:
retracting an outer collar relative to an internal member of a first fluid connector, said outer collar being at least selectively rotatably advanceable and retractable relative to said internal member;
cleaning an outer surface of a distal end of said internal member with said outer collar in a retracted position relative to said internal member, wherein said distal end of said internal member is one of substantially closed and closeable when said fluid connector is disconnected from another fluid connector;
advancing said outer collar of said first fluid connector relative to said internal member thereof to an advanced position;
interconnecting said outer collar of said first fluid connector to a second fluid connector with said outer collar in said advanced position, wherein said second fluid connector includes a tubular member; and,
opening a distal end of a fluid passageway extending through at least a portion of said internal member of said first fluid connector by forcibly penetrating a distal end of said tubular member through a resilient member of said internal member, wherein a fluid interconnection is established.

2. A method for handling a first fluid connector as recited in claim 1, wherein a distal end of said internal member is at least substantially flush with a distal end of said outer collar when said collar is in said retracted position relative thereto.

3. A method for handling a first fluid connector as recited in claim 2, wherein a distal portion of said internal member projects beyond a distal end of said outer collar and is thereby exposed when said outer collar is in said retracted position relative thereto.

4. A method for handling a first fluid connector as recited in claim 3, wherein the exposed distal portion of the internal member includes the distal end and an adjoining sidewall portion, and wherein said cleaning step includes:
contacting the distal end and adjoining sidewall portion of the exposed distal portion with a disinfectant.

5. A method for handling a first fluid connector as recited in claim 4, wherein said distal end of said internal member includes a substantially continuous surface that extends across the entirety of the distal end when said fluid connector is disconnected from a another fluid connector.

6. A method for handling a first fluid connector as recited in claim 1, wherein said retracting step is completed by a first hand of a user, and wherein said cleaning step is completed by a second hand of said user.

7. A method for handling a first fluid connector as recited in claim 1, wherein said interconnecting step includes:
rotating said outer collar of said first fluid connector relative to said second fluid connector.

8. A method for handling a first fluid connector as recited in claim 7, wherein said rotating step includes:
engaging an internally threaded surface of said outer collar of said first fluid connector with an externally threaded surface of the second fluid connector.

9. A method for handling a first fluid connector as recited in claim 7, wherein said rotating step includes:
engaging an externally threaded surface of said outer collar of said first fluid connector with an internally threaded surface of the second fluid connector.

10. A method for handling a first fluid connector as recited in claim 1, wherein said interconnecting step includes:
rotating said outer collar of said first fluid connector to an initial interconnection position relative to said second fluid connector, wherein a mechanical interconnection is made prior to the opening step; and,
rotating the outer collar of the first fluid connection from the initial interconnection position to an advanced interconnection position, wherein said fluid interconnection is established.

11. A method for handling a first fluid connector as recited in claim 1, wherein said internal member includes a first member having at least a portion of said fluid passageway extending therethrough, wherein said resilient member is disposed about a distal end of the first member, and wherein said opening step includes:
forcibly penetrating a distal end of the first member through the resilient member.

12. A method for handling a first fluid connector as recited in claim 1, wherein said cleaning step further includes:
cleaning a distal end of said second fluid connector prior to said interconnection step.

13. A method for handling a first fluid connector as recited in claim 12, wherein the distal end of said internal member and the distal end of said second fluid connector are each substantially closed during said cleaning step.

14. A method for handling a first fluid connector as recited in claim 13, wherein a distal portion of the internal member projects beyond a distal end of the outer collar and is thereby exposed when the outer collar is in the retracted position, and wherein said cleaning step includes:
contacting the exposed distal portion with a disinfectant.

15. A method for handling a first fluid connector, comprising:
retracting an outer collar relative to an internal member of a first fluid connector, said outer collar being at least selectively rotatably advanceable and retractable relative to said internal member;
cleaning an outer surface of a distal end of said internal member with said outer collar in a retracted position relative to said internal member, wherein said distal end of said internal member is one of substantially closed and closeable when said fluid connector is disconnected from another fluid connector;
interconnecting the first fluid connector to a second fluid connector by rotatably advancing the outer collar with respect to the internal member; and
disconnecting the first fluid connector from the second fluid connector by rotatably retracting the outer collar with respect to the internal member from an advanced interconnection position to an initial interconnection position, wherein a mechanical interconnection is maintained between the first fluid connector and the second fluid connector and said fluid interconnection between the first fluid connector and the second fluid connector is terminated, and further rotatably retracting the outer collar with respect to the internal member, wherein said first fluid connector and said second fluid connector mechanically disconnect.

16. A method for handling a first fluid connector as recited in claim 15, wherein said interconnecting step includes:
rotating the outer collar of the first fluid connector to said initial interconnection position relative to the second fluid connector, wherein a mechanical interconnection is made prior to establishing a said fluid interconnection; and rotating the outer collar of the first fluid connection from the initial interconnection position to said advanced interconnection position, wherein said fluid interconnection is established between the first fluid connector and the second fluid connector.

17. A method for handling a first fluid connector as recited in claim 15, further comprising:
repeating said retracting, cleaning, interconnecting, and disconnecting steps.

18. A method for handling a first fluid connector, comprising:
retracting an outer collar relative to an internal member of a first fluid connector;
cleaning an outer surface of a distal end of said internal member with said outer collar in a retracted position relative to said internal member;
advancing said outer collar of said first fluid connector relative to said internal member thereof to an advanced position;
interconnecting said outer collar of said first fluid connector to a second fluid connector with said outer collar in said advanced position, wherein said interconnecting step includes:
rotating said outer collar of said first fluid connector to an initial interconnection position relative to said second fluid connector, wherein a mechanical interconnection is made prior to establishing a fluid interconnection; and,
rotating the outer collar of the first fluid connection from the initial interconnection position to an advanced interconnection position, wherein said fluid interconnection is established between said first fluid connector and said second fluid connector.

19. A method for handling a first fluid connector as recited in claim 18, wherein said fluid interconnection includes:
opening a distal end of a fluid passageway extending through at least a portion of said internal member of said first fluid connector.

20. A method for handling a first fluid connector as recited in claim 19, wherein said internal member includes a first member having at least a portion of said fluid passageway extending therethrough, and a resilient second member disposed about a distal end of the first member, and wherein said opening step includes:
forcibly penetrating a distal end of the first member through the second member.

21. A method for handling a first fluid connector, comprising:
retracting an outer collar relative to an internal member of a first fluid connector;
cleaning an outer surface of a distal end of said internal member with said outer collar in a retracted position relative to said internal member;
advancing said outer collar of said first fluid connector relative to said internal member thereof to an advanced position;
interconnecting said outer collar of said first fluid connector to a second fluid connector with said outer collar in said advanced position, wherein said second fluid connector includes a tubular member;
establishing a fluid interconnection between said first fluid connector and said second fluid connector by opening a distal end of a fluid passageway extending through at least a portion of said internal member of said first fluid connector, wherein said opening includes forcibly penetrating a distal end of said tubular member through a resilient member of said first fluid connector.

* * * * *